US012697155B2

(12) United States Patent
Zenker et al.

(10) Patent No.: US 12,697,155 B2
(45) Date of Patent: Aug. 4, 2026

(54) ANATOMICAL PROXIMAL HUMERUS OSTEOSYNTHESIS DEVICES AND SYSTEMS AND METHODS OF USE THEREOF

(71) Applicant: DePuy Synthes Products, Inc., Raynham, MA (US)

(72) Inventors: Martin Zenker, West Chester, PA (US); Sol Posada, West Chester, PA (US); Daniel Andermatt, West Chester, PA (US); Marcel Schweizer, West Chester, PA (US); André Galm, West Chester, PA (US); Martin Jaeger, West Chester, PA (US); Stefaan Nijs, West Chester, PA (US); Harry Hoyen, West Chester, PA (US); Frank Beeres, West Chester, PA (US); Simon Lambert, West Chester, PA (US); Chunyan Jiang, West Chester, PA (US); Joyce Koh, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 129 days.

(21) Appl. No.: 18/781,067

(22) Filed: Jul. 23, 2024

(65) Prior Publication Data

US 2025/0049483 A1     Feb. 13, 2025

Related U.S. Application Data

(60) Provisional application No. 63/518,442, filed on Aug. 9, 2023.

(51) Int. Cl.
A61B 17/80          (2006.01)
A61B 17/17          (2006.01)
(Continued)

(52) U.S. Cl.
CPC ...... *A61B 17/8061* (2013.01); *A61B 17/8605* (2013.01); *A61B 17/1728* (2013.01);
(Continued)

(58) Field of Classification Search
CPC ............ A61B 17/8061; A61B 17/8057; A61B 17/8605; A61B 17/80; A61B 17/8052;
(Continued)

(56) References Cited

U.S. PATENT DOCUMENTS 8,535,313 B1 * 9/2013 Masson .................. A61B 17/80
                                               606/232
9,381,053 B2 * 7/2016 Parsons .................. A61B 17/82
(Continued)

FOREIGN PATENT DOCUMENTS

| EP | 2730244 A1 | 5/2014 |
| EP | 3202348 B1 | 1/2020 |
| WO | 2013073994 A1 | 5/2013 |

OTHER PUBLICATIONS

International Search Report and Written Opinion dated Nov. 28, 2024, in PCT/IB2024/057266, filed Jul. 26, 2024.

*Primary Examiner* — Marcela I. Shirsat
(74) *Attorney, Agent, or Firm* — Dunlap Codding, P.C.

(57) ABSTRACT

Anatomical proximal humerus osteosynthesis bone plate devices, as well as kits and systems containing same, are disclosed. The bone plate devices are configured and adapted for attachment to a proximal humerus. The kits include at least two bone plate devices that differ from one another in at least one structural and/or size characteristic. Also disclosed are methods of use thereof.

20 Claims, 21 Drawing Sheets

(51) Int. Cl.

| | |
|---|---|
| *A61B 17/32* | (2006.01) |
| *A61B 17/56* | (2006.01) |
| *A61B 17/58* | (2006.01) |
| *A61B 17/84* | (2006.01) |
| *A61B 17/86* | (2006.01) |
| *A61B 17/88* | (2006.01) |

(52) U.S. Cl.
CPC ..................... *A61B 17/1739* (2013.01); *A61B 2017/320052* (2013.01); *A61B 2017/564* (2013.01); *A61B 17/58* (2013.01); *A61B 17/8052* (2013.01); *A61B 17/8057* (2013.01); *A61B 17/808* (2013.01); *A61B 17/848* (2013.01); *A61B 17/8897* (2013.01)

(58) Field of Classification Search
CPC ..... A61B 17/808; A61B 17/86; A61B 17/861; A61B 17/848; A61B 17/8625; A61B 17/8897; A61B 17/90; A61B 17/17; A61B 17/1728; A61B 17/1739; A61B 17/1732; A61B 17/58; A61B 2017/564; A61B 2017/320052
USPC ......... 606/280, 86 R, 281, 286, 291, 87, 96, 606/86 B, 902, 915
See application file for complete search history.

(56) References Cited

U.S. PATENT DOCUMENTS

| | | | |
|---|---|---|---|
| 10,238,438 B2 | 3/2019 | Shah et al. | |
| 10,966,766 B2 | 4/2021 | Shah et al. | |
| 11,426,220 B2 * | 8/2022 | Courtney, Jr. | ....... A61B 17/808 |
| 2009/0326591 A1 | 12/2009 | Spencer, Jr. | |
| 2011/0224736 A1 | 9/2011 | Humphrey | |
| 2017/0042596 A9 | 2/2017 | Mighell et al. | |
| 2021/0038271 A1 | 2/2021 | Hamel et al. | |
| 2023/0190345 A1 | 6/2023 | Langdale et al. | |

* cited by examiner

Bone Size

| count | 570.000000 |
|-------|------------|
| mean | 19.752556 |
| std | 3.080716 |
| min | 13.268741 |
| 5% | 15.384513 |
| 10% | 16.065932 |
| 25% | 17.324070 |
| 50% | 19.593648 |
| 75% | 21.651424 |
| 90% | 23.879910 |
| 95% | 25.062807 |
| max | 33.338360 |

| count | 570.000000 |
|-------|------------|
| mean | 26.682940 |
| std | 2.949085 |
| min | 17.816252 |
| 5% | 22.175284 |
| 10% | 22.910959 |
| 25% | 24.301593 |
| 50% | 26.822331 |
| 75% | 28.770818 |
| 90% | 30.425425 |
| 95% | 31.497986 |
| max | 35.425850 |

A.

Small          Medium          Large

B.

Small                          Medium                          Large

C.

Small                    Medium                    Large

Size (Bone Size which Plate Fits to)

ANATOMICAL PROXIMAL HUMERUS OSTEOSYNTHESIS DEVICES AND SYSTEMS AND METHODS OF USE THEREOF

CROSS REFERENCE TO RELATED APPLICATIONS/INCORPORATION BY REFERENCE STATEMENT

This application claims benefit under 35 USC § 119(e) of U.S. Ser. No. 63/518,442, filed Aug. 9, 2023. The entire contents of the above-referenced patent application(s) are hereby expressly incorporated herein by reference.

STATEMENT REGARDING FEDERALLY SPONSORED RESEARCH OR DEVELOPMENT

Not Applicable.

BACKGROUND

Fractured long bones in the arm are often treated using rigid metal or plastic bone plates which may be fixed to the bone or bone fragments using screws or similar fasteners. The screws or other fasteners are attached to the bone on each side of the fracture through apertures in the bone plate, and the screws or other fasteners engage the bone and lock into the bone plate or provide a compressive force against the bone plate. The bone plate may also be provided with suture-receiving holes or structures that allow tendons or ligaments normally connected to the damaged bone to be fixed to the bone plate with sutures, anchoring the tendons or ligaments in place.

However, many operative and post-operative challenges are encountered with internal fixation of the proximal humerus. Operative Challenges encountered include (but are not limited to): poor fixation quality (especially in patients with poor bone quality); a limited ability to address the posterior greater tuberosity and superior greater tuberosity fragments; poor calcar screw positioning, which leads to reduced overall construct stability; poor plate fit in the global population, including small-statured patients; rotator cuff management challenges (such as, but not limited to, difficulty suturing the rotator cuff to the plate after plate insertion); axillary nerve interference; plate interference with deltoid insertion when implanting long plates, which causes either prolonged surgery due to need for plate contouring and/or deltoid elevation technique, or inadequate plate placement if release or plate contouring is avoided; procedural complexity, including difficulty with visualization and reduction; and challenges with screw placement in periprosthetic fractures. Post-operative challenges encountered following internal fixation of the proximal humerus include (but are not limited to): *varus* collapse due to poor fixation quality; superior plate impingement with acromion; subchondral bone penetration in humeral head by screws due to subsidence; postoperative displacement of the posterior greater tuberosity and superior greater tuberosity; limited range of motion due to inadequately addressed rotator cuff suturing; and functional deficits due to deltoid elevation/release that can be necessary for insertion of long plates.

Therefore, there is a need in the art for new and improved devices and methods of using same for fixation of proximal humeral fractures. It is to such devices, as well as kits and systems containing same and methods of producing and using same, that the present disclosure is directed.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings:

FIG. 18 is a perspective view from a side of the bone plate device of FIG. 16.

FIG. 20 is a perspective view from the bone-facing surface of the bone plate device of FIG. 19.

DETAILED DESCRIPTION

Figure 1:
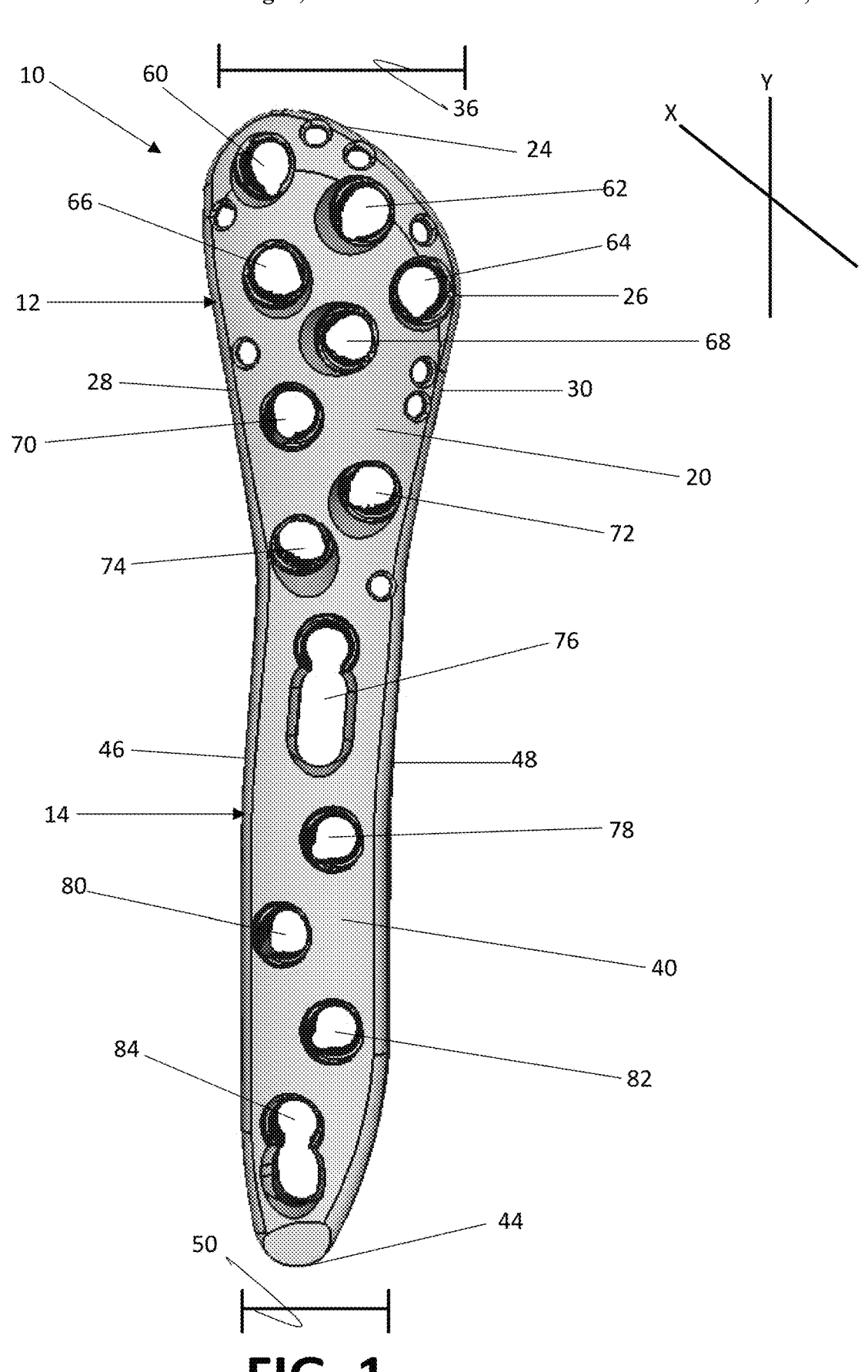
FIG. 1 is a perspective view of one non-limiting embodiment of a proximal humerus bone plate device constructed in accordance with the present disclosure.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary-not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infectious control described herein are those well-known and commonly used in the art. Standard techniques are used for infection diagnostic and therapeutic applications.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and, unless explicitly stated otherwise, is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps. For example, a process, method, article, or apparatus that comprises a list of elements is not necessarily limited to only those elements but may include other elements not expressly listed or inherently present therein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example (but not by way of limitation), when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with," "coupled to," and "connected to" include both direct association/coupling/connection of two elements to one another as well as indirect association/coupling/connection of two elements to one another. When two elements are indirectly associated/coupled/connected to one another, one or more intervening elements may be present therebetween. Non-limiting examples of intervening elements include washers, sleeves, fasteners, nuts, bolts, anchors, nails, inserts, rivets, bonding materials, and the like.

As used herein, the term "patient" or "subject" is meant to include all organisms, whether alive or dead, including any species having soft tissues and bones. For example, a system according to the inventive concepts disclosed herein may be applied to the bone of a living human, horse, cow, sheep, cat, dog, and the like.

The terms "bone fastener," "bone fixation element," and "bone screw" are used interchangeably herein and refer to an element used to secure a bone plate to a bone.

The terms "through hole," "fastener hole," and "screw hole" are used interchangeably herein and refer to an opening extending through a bone plate and through which a bone fastener/bone fixation element/bone screw can be inserted for securing the bone plate to the bone. The term "fastener hole" includes single holes as well as combination holes (i.e., combi-holes).

Turning now to the present disclosure, various non-limiting embodiments of an anatomical proximal humerus osteosynthesis plate system for the treatment of proximal humeral fractures, mal- and non-unions, with and without extension into the humeral shaft, are disclosed. At least one bone plate is fixed to the lateral surface of the proximal humerus (the greater tuberosity) and provide options for screw fixation into the humeral head and shaft. The design of the plates is based on morphological analysis of the proximal humerus. A system of proximal humerus osteosynthesis plates, including multiple shapes and/or sizes of plate heads, is disclosed, where the plate head sizes are determined by correlation of multiple anatomical parameters of the target patient population. The plate head shapes are determined by the footprint to be covered on the greater tuberosity of the proximal humerus to treat specific indications. Target patient populations are stratified based on the maximum width of the greater tuberosity of the humerus to provide the system of proximal humerus osteosynthesis plates that will most closely correlate to the size and shape of the multiple anatomical parameters of the target patient population.

Certain non-limiting embodiments of the present disclosure are directed to a bone plate device configured and adapted to be attached to a surface of a proximal humerus for promoting healing of a fracture in the humerus of a subject. The bone plate device comprises a head region and a shaft region. The head region is configured to conform to and adapted to be attached to a greater tuberosity of the proximal humerus, while the shaft region is configured and adapted to be attached to a shaft of the humerus.

The shaft region comprises an elongated portion extending along a longitudinal axis and has an upper surface, an opposed bone-facing surface, and a lower edge. The shaft region also has a first side edge and a second side edge with a width extending therebetween. In addition, the shaft region has at least one fastener hole extending through the upper surface and bone-facing surface for receiving at least one bone fastener for securing the shaft region of the bone plate device to the shaft of the humerus.

The head region extends at a lateral angle relative to the longitudinal axis and has an upper surface, an opposed bone-facing surface, an upper boundary edge with a curvature, and a first side edge and a second side edge that each extend from the upper boundary edge. The head region has a maximum width extending between the first or second side edge and a lower end of the upper boundary edge. In addition, the head region comprises a plurality of fastener holes extending through the upper surface and bone-facing surface for receiving bone fasteners for securing the head region to the greater tuberosity such that the upper edge curvature of the head region is disposed substantially adjacent an upper curvature of the greater tuberosity.

The head region may be provided with any size and shape that allows the head region to closely correlate to the size and shape of multiple anatomical parameters of the greater tuberosity of the humerus across a target patient population and thereby sufficiently secure the bone plate device to the humerus during a sufficient period of healing. The plate head sizes are determined by correlation of multiple anatomical parameters of the target patient population, while the plate head shapes are determined by the footprint to be covered on the greater tuberosity of the proximal humerus to treat specific indications.

In certain particular (but non-limiting) embodiments, the head region of the bone plate device has a maximum width of about 15 mm, about 15.5 mm, about 16 mm, about 16.5 mm, about 17 mm, about 17.5 mm, about 18 mm, about 18.5 mm, about 19 mm, about 19.5 mm, about 20 mm, about 20.5 mm, about 21 mm, about 21.5 mm, about 22 mm, about 22.5 mm, about 23 mm, about 23.5 mm, about 24 mm, about 24.5 mm, about 25 mm, about 25.5, mm, about 25.6 mm, about 26 mm, about 26.5 mm, about 27 mm, about 27.5 mm, about 28 mm, about 28.2 mm, about 28.5 mm, about 28.9, about 29 mm, about 29.5 mm, about 30 mm, about 30.5 mm, about 31 mm, about 31.5 mm, about 32 mm, about 32.5 mm, about 33 mm, about 33.5 mm, about 34 mm, about 34.5 mm, about 35 mm, about 35.5, mm, about 36 mm, about 36.5 mm, about 37 mm, and the like, as well as a range formed from any two of the above values (i.e., a range of from about 15 mm to about 37 mm, a range of from about 17 mm to about 36 mm, a range of from about 17.5 mm to about 35.5 mm, a range of from about 22 mm to about 32 mm, a range of from about 20 mm to about 26 mm, a range of from about 21.5 mm to about 25 mm, a range of from about 22 mm to about 29 mm, a range of from about 22.5 mm to about 25 mm, a range of from about 24 mm to about 29 mm, a range of from about 24.5 mm to about 28 mm, a range of from about 25.5 mm to about 28 mm, a range of from about 27 mm to about 36 mm, a range of from about 27 mm to about 31.5 mm, a range of from about 28.5 mm to about 31.5 mm, a range of from about 31 mm to about 36 mm, a range of from about 22.5 mm to about 28.9 mm, etc.). In a particular (but non-limiting) embodiment, the head region of the bone plate device has a maximum width of about 22 mm, about 22.5 mm, about 25.5 mm, about 25.6 mm, about 26.0, about 28.2 mm, about 28.5 mm, about 28.9 mm, or about 29 mm.

In certain particular (but non-limiting) embodiments, the head region of the bone plate device has a maximum height of about 10 mm, about 10.1 mm, about 10.2 mm, about 10.3 mm, about 10.4 mm, about 10.5 mm, about 10.6 mm, about 10.7 mm, about 10.8 mm, about 10.9 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, about 20 mm, about 20.5 mm, about 21 mm, about 21.5 mm, about 22 mm, about 22.5 mm, about 23 mm, about 23.5 mm, about 24 mm, about 24.5 mm, about 25 mm, about 25.5, mm, about 25.6 mm, about 26 mm, about 26.1 mm, about 26.2 mm, about 26.3 mm, about 26.4 mm, about 26.5 mm, about 26.6 mm, about 26.7 mm, about 26.8 mm, about 26.9 mm, about 27 mm, about 27.5 mm, about 28 mm, about 28.1 mm, about 28.2 mm, about 28.3 mm, about 28.4 mm, about 28.5 mm, about 28.6 mm, about 28.7 mm, about 28.8 mm, about 28.9 mm, about 29 mm, about 29.5 mm, about 30 mm, about 30.1 mm, about 30.2 mm, about 30.3 mm, about 30.4 mm, about 30.5 mm, about 30.6 mm, about 30.7 mm, about 30.8 mm, about 30.9 mm, about 31 mm, about 31.5 mm, about 32 mm, and the like, as well as a range formed from any two of the above values (i.e., a range of from about 10 mm to about 31 mm, a range of from about 10 mm to about 30.8 mm, a range of from about 10.4 mm to about 28.5 mm, a range of from about 10.6 mm to about 26.8 mm, etc.).

In certain particular (but non-limiting) embodiments, the head region has a ratio of maximum width to height of about 1.15:1, about 1.16:1, about 1.17:1, about 1.18:1, about 1.19:1, about 1.20:1, about 1.21:1, about 1.22:1, about 1.23:1, about 1.24:1, about 1.25:1, about 1.26:1, about 1.27:1, about 1.28:1, about 1.29:1, about 1.30:1, about 1.31:1, about 1.32:1, about 1.33:1, about 1.34:1, about 1.35:1, about 1.36:1, about 1.37:1, about 1.38:1, about 1.39:1, about 1.40:1, about 1.41:1, about 1.42:1, about 1.43:1, about 1.44:1, about 1.45:1, about 1.46:1, about 1.47:1, about 1.48:1, about 1.49:1, about 1.50:1, about 1.51:1, about 1.52:1, about 1.53:1, about 1.54:1, or about 1.55:1. In certain particular (but non-limiting) embodiments, the ratio of maximum width to height falls within a range of two of the above values (i.e., a range of from about 1.15:1 to about 1.55:1, a range of from about 1.2:1 to about 1.5:1, a range of from about 1.2:1 to about 1.4:1, a range of from about 1.25:1 to about 1.35:1, a range of from about 1.27:1 to about 1.35:1, a range of from about 1.28:1 to about 1.33:1, a range of from about 1.29:1 to about 1.31:1, etc.).

In certain particular (but non-limiting) embodiments, the head region has a radius of curvature across a width of the head region (i.e., a maximum radius) of about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.3 mm, about 17.4 mm, about 17.5 mm, about 18 mm, about 18.5 mm, about 19 mm, about 19.5 mm, about 19.7 mm, about 20 mm, about 20.4 mm, about 20.5 mm, about 21 mm, about 21.5 mm, about 21.9 mm, about 22 mm, about 22.1 mm, about 22.5 mm, about 23 mm, about 23.5 mm, about 24 mm, about 24.5 mm, about 25 mm, about 25.5, mm, about 26 mm, about 26.5 mm, about 27 mm, about 27.5 mm, about 28 mm, about 28.5 mm, about 29 mm, about 29.5 mm, about 30 mm, about 30.5 mm, about 31 mm, about 31.5 mm, about 32 mm, about 32.5 mm, about 33 mm, about 33.5 mm, about 34 mm, about 34.5 mm, about 35 mm, and the like, as well as a range formed from any two of the above values (i.e., a range of from about 12 mm to about 34 mm, a range of from about 13 mm to about 34 mm, a range of from about 15 mm to about 25 mm, a range of from about 13 mm to about 24 mm, a range of from about 16 mm to about 29 mm, a range of from about 17 mm to about 23 mm, a range of from about 18 mm to about 33 mm, a range of from about 13.5 mm to about 24 mm, a range of from about 16 mm to about 28.5 mm, a range of from about 18.5 mm to about 33 mm, a range of from about 17.3 mm to about 22.1 mm, etc.). In a particular (but non-limiting) embodiment, the head region of the bone plate device has a maximum radius of about 17.3 mm, about 17.4 mm, about 17.5 mm, about 19.5 mm, about 19.7 mm, about 20.4 mm, about 21.5 mm, about 21.9 mm, or about 22.1 mm.

In certain particular (but non-limiting) embodiments, the size and configuration of the bone plate device is based on a plurality of morphological measurements of the greater tuberosity of the humerus. For example (but not by way of limitation), the morphological measurements may comprise a greater tuberosity top point, a greater tuberosity/shaft connection point, a greater tuberosity maximum anterior point, and a greater tuberosity maximum posterior point. Based on these points, the height of the head region is calculated as a distance between the greater tuberosity top point and the greater tuberosity/shaft connection point (referred to as "dyHeadmax"), and the maximum width is calculated as a distance between the greater tuberosity maximum anterior point and the greater tuberosity maximum posterior point (referred to as "dxHeadmx (anterior+ posterior)").

The plurality of fastener holes in the head region of the bone plate device may be provided in any pattern or configuration that allows the bone plate device to be anchored to the greater tuberosity of the proximal humerus and function as described herein. For example (but not by way of limitation), the plurality of fastener holes in the head region of the bone plate device may have a pattern comprising an upper row of three holes, a middle row of two holes, and a lower row of two holes. In addition, the pattern may further comprise a fourth row of one or more additional holes.

In addition, the rows of fastener holes in the head region may be disposed at any angle. In certain particular (but non-limiting) embodiments, one or more rows of holes may be disposed along the lateral angle. For example (but not by way of limitation), at least the upper row of holes may be disposed along the lateral angle so as to generally follow the curvature of the upper boundary edge of the head region. In addition (but not by way of limitation), the second, third, and/or fourth (and/or any additional) rows may also be disposed along the lateral angle. Alternatively, at least one of the rows of fastener holes (such as, but not limited to, the third, fourth, and/or any additional rows) may be disposed along a horizontal or longitudinal angle.

The shaft region of the bone plate device includes at least one fastener hole, and the at least one fastener hole may be a single hole or a combination hole (combi-hole). Combi-holes may be provided with any configuration known in the art or otherwise contemplated herein that is adapted to aid in plate positioning, to provide the flexibility of axial compression, and/or to provide locking capability. When multiple fastener holes are present in the shaft region, the plurality may include all single holes, all combi-holes, or a combination of single holes and combi-holes. For example, but not by way of limitation, the shaft region of the bone plate device may include about one fastener hole, about two fastener holes, about three fastener holes, about four fastener holes, about five fastener holes, about six fastener holes, about seven fastener holes, about eight fastener holes, about nine fastener holes, about 10 fastener holes, about 11 fastener holes, about 12 fastener holes, about 13 fastener holes, about 14 fastener holes, about 15 fastener holes, about 16 fastener holes, about 17 fastener holes, about 18 fastener holes, about 19 fastener holes, about 20 fastener holes, about 21 fastener holes, about 22 fastener holes, about 23 fastener holes, about 24 fastener holes, about 25 fastener holes, about 26 fastener holes, about 27 fastener holes, about 28 fastener holes, about 29 fastener holes, about 30 fastener holes, and the like, as well as a range formed of two of the above values (e.g., a range of from about 1 fastener hole to about 30 fastener holes, a range of from about 1 fastener hole to about 25 fastener holes, a range of from about 1 fastener hole to about 20 fastener holes, a range of from about 3 fastener holes to about 13 fastener holes, etc.). In addition, said ranges can include any combination of single fastener holes and combi-holes.

In a particular (but non-limiting) embodiment, the shaft region of the bone plate device may include a plurality of fastener holes extending substantially linearly along the longitudinal axis of the shaft region. The plurality of fastener holes arranged in this manner may be all single fastener holes, all combi-holes, or a combination of single fastener holes and combi-holes. In another particular (but non-limiting) embodiment, the shaft region of the bone plate device may include a plurality of fastener holes extending in any non-linear pattern along the longitudinal axis of the shaft region. The plurality of fastener holes arranged in this manner may be all single fastener holes, all combi-holes, or a combination of single fastener holes and combi-holes.

Certain non-limiting embodiments of the present disclosure are directed to a kit comprising a plurality of any of the bone plate devices disclosed or otherwise contemplated herein. For example, but not by way of limitation, the kit may contain at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, or more bone plate devices. In another non-limiting example, the number of bone plate devices present in the kit may be in a range of two of the above values (e.g., a range of from about 1 to about 20 bone plate devices, a range of from about 1 to about 10 bone plate devices, a range of from about 3 to about 9 bone plate devices, etc.).

At least two or three of the bone plate devices have head regions that have different sizes and/or shapes from one another. That is, the kit may contain two sizes and/or shapes of head regions (i.e., "small" and "large" head regions), wherein these two sizes/shapes of head regions provide a sufficient coverage of the target population. Alternatively, the kit may contain at least three sizes and/or shapes of head regions (i.e., "small," "medium," and "large" head regions), wherein these three sizes/shapes of head regions provide a sufficient coverage of the target population.

In certain particular (but non-limiting) embodiments, the different sizes/shapes of head regions (i.e., "small," "medium," and/or "large" head regions) may have different patterns of fastener holes compared to one another.

In addition, the kit may contain two or more bone plate devices that have the same size/shape head region (i.e., two "small" head region devices). In this instance, these two or more bone plate devices may be identical, or the two or more bone plate devices may differ in other aspects. For example (but not by way of limitation), the lengths of the shaft regions of the two or more devices with the same size/shape head region may differ from one another, and/or the patterns of fastener holes in the head and/or shaft region may differ from one another.

In a certain particular (but non-limiting) embodiment, the kit contains at least two first (i.e., "small") bone plate devices, at least two second (i.e., "medium") bone plate devices, and at least two third (i.e., "large") bone plate devices, wherein the at least two first devices have the same head region shape/size as each other but different shaft region lengths, the at least two second devices have the same head region shape/size as each other but different shaft region lengths, and the at least two third devices have the same head region shape/size as each other but different shaft region lengths. In addition (but not by way of limitation), said kit may contain at least three, four, five, or more second (i.e., "medium") devices, wherein the plurality of second devices has the same head region shape/size as each other but different shaft region lengths from each another. In this manner, the bone plate device size that covers the broadest swath of the population (i.e., the "medium" size) is also provided with the widest selection of shaft region lengths.

In certain particular (but non-limiting) embodiments, when two or more bone plate devices of a particular size (i.e., "small," "medium," "large," etc.) are present, the two or more bone plate devices have different patterns of fastener holes in the head and/or shaft region. In a particular (but non-limiting) embodiment, the two or more bone plate devices of a particular size have different patterns of fastener holes in the head and shaft regions.

In certain particular (but non-limiting) embodiments, the "small" device(s) has/have a ratio of maximum width to height in a range of from about 1.40:1 to about 1.44:1, the "medium" device(s) has/have a ratio of maximum width to height in a range of from about 1.38:1 to about 1.42:1, and the "large" device(s) has/have a ratio of maximum width to height in a range of from about 1.36:1 to about 1.40:1. In another particular (but non-limiting) embodiment, the "small" device(s) has/have a ratio of maximum width to height in a range of from about 1.41:1 to about 1.43:1, the "medium" device(s) has/have a ratio of maximum width to height in a range of from about 1.39:1 to about 1.41:1, and the "large" device(s) has/have a ratio of maximum width to height in a range of from about 1.37:1 to about 1.39:1. In a particular (but non-limiting) embodiment, the "small" device(s) has/have a ratio of maximum width to height of about 1.42:1, the "medium" device(s) has/have a ratio of maximum width to height in of about 1.40:1, and the "large" device(s) has/have a ratio of maximum width to height of about 1.38:1.

In certain particular (but non-limiting) embodiments, the bone plate devices present in the kits of the present disclosure have a maximum width that is at the same height as measured from a "dyHeadmax," as described in detail herein.

In certain non-limiting embodiments, the kits of the present disclosure may include one or more bone fasteners configured to matingly engage one or more fastener holes on the bone plate device and thereby secure the bone plate device to the humerus. For example (but not by way of limitation), the kits may further include: a plurality of bone fasteners, each configured to matingly engage at least one of the plurality of fastener holes in the head region of the device; and/or at least one bone fastener configured to matingly engage at least one fastener hole in the shaft region of the device. Non-limiting examples of bone fasteners that may be utilized in accordance with the present disclosure include screws, pins, nails, bolts, anchors, rivets, and the like, as well as any combinations thereof.

In addition, the kit may further contain one or more other component(s) or reagent(s) that may be utilized with the bone plate devices and bone fasteners in accordance with the present disclosure. For example (but not by way of limitation), the kit may further comprise at least one instrument utilized in placing the bone plate device, such as, but not limited to, a guide block, an aiming device, a Kirschner wire, a sizing template, a sharp hook, a sleeve, a washer, a nut, a length probe, a depth gauge, a drill guide, a drill bit, a screwdriver (or portion thereof), a ratchet, a torque limiter, an extraction screw, and the like, as well as any combinations thereof. The nature of these additional component(s)/reagent(s) will depend upon various factors, and identification thereof is well within the skill of one of ordinary skill in the art; therefore, no further description thereof is deemed necessary.

Also, the various components/reagents present in the kit may each be in separate containers/compartments, or various components/reagents can be combined in one or more containers/compartments. That is, the osteosynthesis system may be provided partially or fully assembled, or the osteosynthesis system may be provided in a disassembled form such that the bone plate devices and bone fasteners are packaged separately within the kit. In addition, the kit may include a set of written instructions explaining how to use the kit. A kit of this nature can be used in any of the methods described or otherwise contemplated herein.

Certain non-limiting embodiments of the present disclosure are directed to a method of promoting healing of a fracture in the humerus of a subject. The method comprises the steps of placing any of the bone plate devices disclosed or otherwise contemplated herein adjacent a surface of the fractured proximal humerus, and securing the bone plate device to the fractured humeral bone by inserting bone fasteners through the fastener holes in the bone plate device and through the bone plate device into the bone. In this manner, the head region of the bone plate device is attached to a greater tuberosity of the proximal humerus, and the shaft region of the bone plate device is attached to a shaft of the humerus. Also, the head region is secured to the greater tuberosity such that the upper edge curvature of the head region is disposed substantially adjacent an upper curvature of the greater tuberosity.

In certain particular (but non-limiting) embodiments, the method further comprises the step of selecting the bone plate device from any of the kits disclosed or otherwise contemplated herein.

In addition, in certain particular (but non-limiting) embodiments, the method may further comprise the step of performing a plurality of morphological measurements of the humerus to determine which bone plate device to select. For example (but not by way of limitation), the plurality of morphological measurements may comprise determining a greater tuberosity top point, a greater tuberosity/shaft connection point, a greater tuberosity maximum anterior point, and a greater tuberosity maximum posterior point. Based on these measurements, the height of the head region is calculated as a distance between the greater tuberosity top point and the greater tuberosity/shaft connection point, and the maximum width is calculated as a distance between the greater tuberosity maximum anterior point and the greater tuberosity maximum posterior point.

These morphological measurements may be performed by any methods known in the art, such as but not limited to, various imaging and/or manual measurement methods.

For each of the methods described herein, two or more steps may be performed simultaneously or wholly or partially sequentially. In addition, one or more of the steps may be performed immediately following a prior step, and/or a period of time may pass in between two or more steps.

Further, changes can be made in the order or sequence of steps, and one or more steps may be repeated, as desired, for any of the methods disclosed or otherwise contemplated herein.

Figure 2:
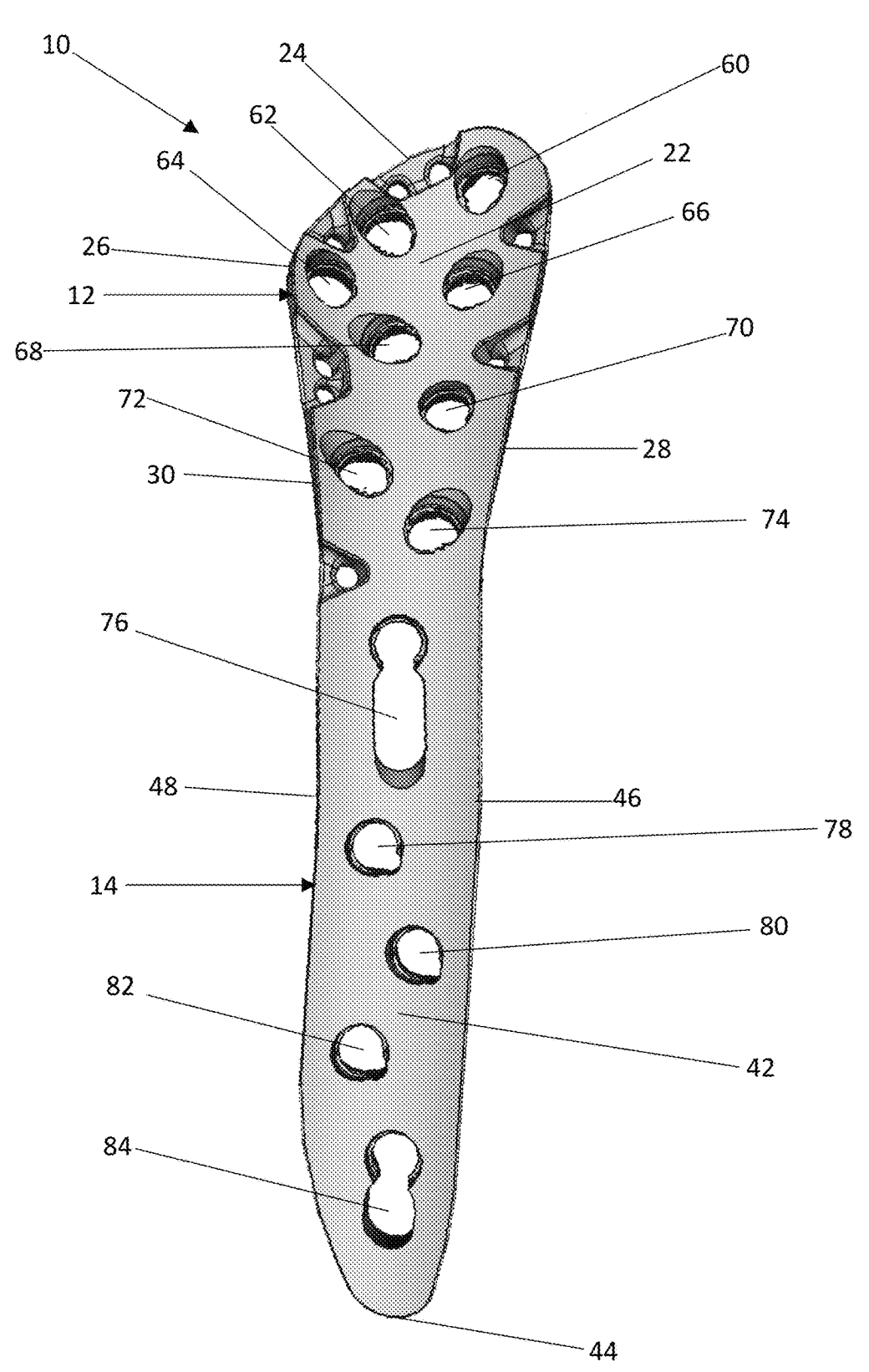
FIG. 2 is a perspective view from the bone-facing surface of the bone plate device of FIG. 1.
Figure 3:
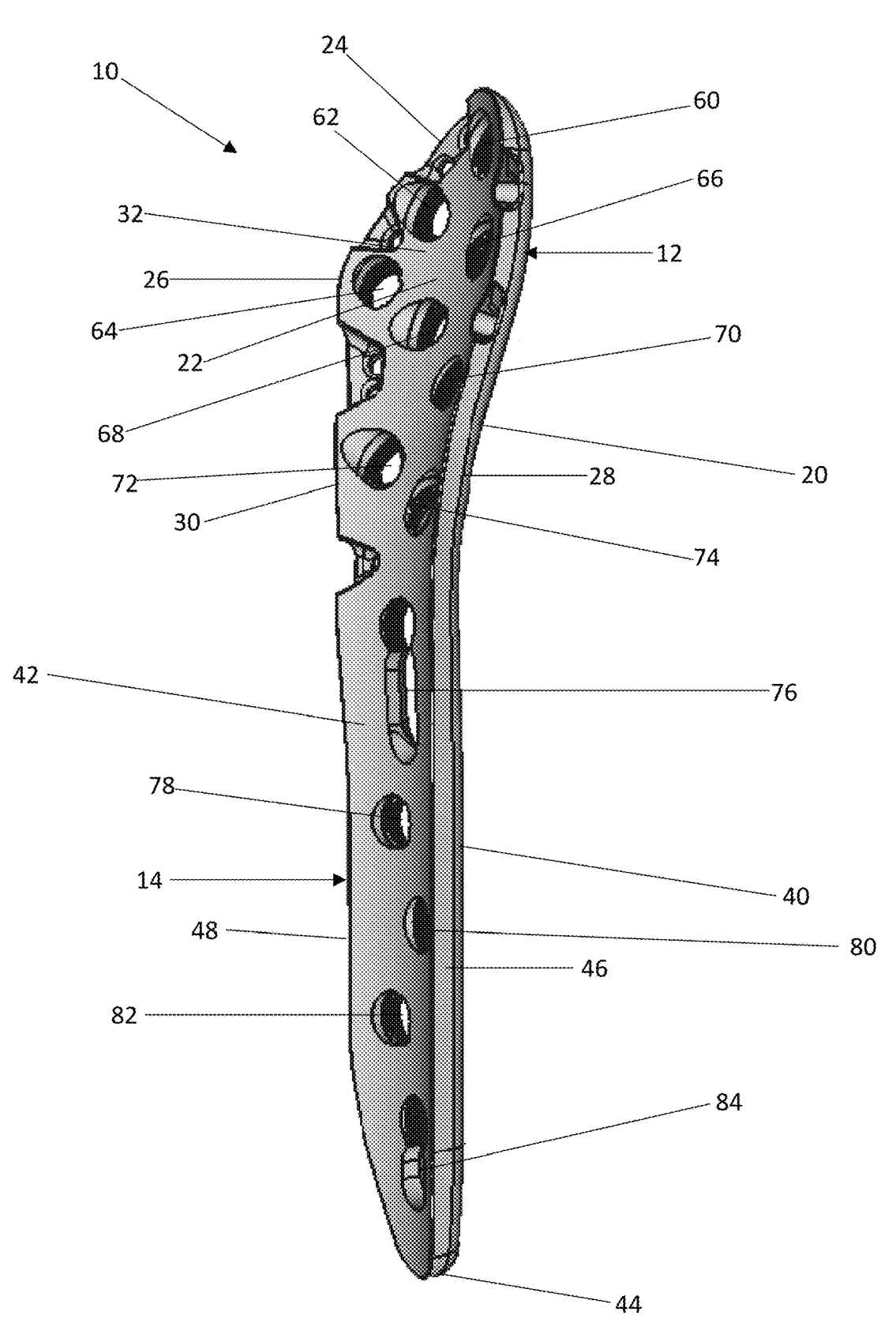
FIG. 3 is a perspective view from a side of the bone plate device of FIG. 1.

Turning now to the Drawings, FIGS. 1-3 illustrates one non-limiting embodiment of a proximal humeral bone plate device 10 constructed in accordance with the present disclosure. The bone plate device 10 comprises a head region 12 and a shaft region 14. The head region 12 is configured to conform to and adapted to be attached to a greater tuberosity of the proximal humerus, while the shaft region 14 is configured and adapted to be attached to a shaft of the humerus.

The head region 12 extends at a lateral angle X relative to a longitudinal axis Y and has an upper surface 20, an opposed bone-facing surface 22, an upper boundary edge 24 with a curvature and a lower end 26, a first side edge 28, and a second side edge 30, wherein each of the first and second side edges 28 and 30 extends from the upper boundary edge 24 (for example, but not by way of limitation, FIG. 1 illustrates the second side edge 30 as extending from the lower end 26 of the upper boundary edge 24). The curved bone-facing surface 22 has a radius of curvature 34 that approximately conforms to a shape of a greater tuberosity of a proximal humerus. The head region 12 also has a maximum width 36 extending between the lower end 26 of the upper boundary edge 24 and the opposing side edge (in this case, the first side edge 28).

The shaft region 14 comprises an elongated portion extending along the longitudinal axis Y and has an upper surface 40 (that is contiguous with the upper surface 20 of the head region 12), an opposed bone-facing surface 42 (that is contiguous with the bone-facing surface 22 of the head region 12), a lower edge 44, a first side edge 46 (that is contiguous with the first side edge 28 of the head region 12), a second side edge 48 (that is contiguous with the second side edge 30 of the head region 12), and a width 50 extending between the first and second side edges 46 and 48.

In addition, each of the head and shaft regions 12 and 14 has at least one fastener hole extending through the upper and lower surfaces thereof; each of the fastener holes is configured for receiving a bone fastener (such as, but not limited to, a screw, pin, rod, nail, or other type of fixation device) for securing the bone plate device 10 to the humerus. For example (but not by way of limitation), the head region 12 is depicted as having fastener holes 60, 62, 64, 66, 68, 70, 72, and 74 extending through the upper surface 20 and bone-facing surface 24 of the head region 12 for receiving bone fasteners for securing the head region 12 to the greater tuberosity such that the upper edge curvature of the head region is disposed substantially adjacent an upper curvature of the greater tuberosity. The fastener holes 60, 62, and 64 are depicted as being generally disposed in a row along the lateral angle X so as to generally follow the curvature of the upper boundary edge 24 of the head region 12. In addition (but not by way of limitation), the fastener holes 66 and 68 are depicted as being generally disposed in a row along the lateral angle X and approximately along a mid-section of the head region 12, while the fastener holes 70 and 72 are depicted as also being generally disposed in a row along the lateral angle X and along a lower portion of the head region 12. However, this depiction of row patterns and disposal along a particular angle is for purposes of illustration only; it will be understood that any of the rows of fastener holes may assume any patterns and be disposed along a horizontal or longitudinal angle.

In addition, the shaft region 14 is depicted as having fastener holes 76, 78, 80, 82, and 84 extending through the upper surface 40 and bone-facing surface 42 of the shaft region 14 for receiving bone fasteners for securing the shaft region 14 of the bone plate device 10 to the shaft of the humerus.

However, the number and pattern of fastener holes depicted in FIGS. 1-3 is for purposes of illustration only; it will be understood that the bone plate devices of the present disclosure can be provided with any number of fastener holes and any pattern of fastener holes that allow the bone plate devices to function in accordance with the present disclosure.

Also, one or more of the fastener holes may be provided with one or more features or structures that allow the fastener holes to interact with the bone fasteners and aid in securing the bone plate device 10 to the humerus. For example (but not by way of limitation), when one or more of the bone fasteners is a screw, the corresponding fastener hole may be provided with threading around the edges of the opening.

Figure 4:
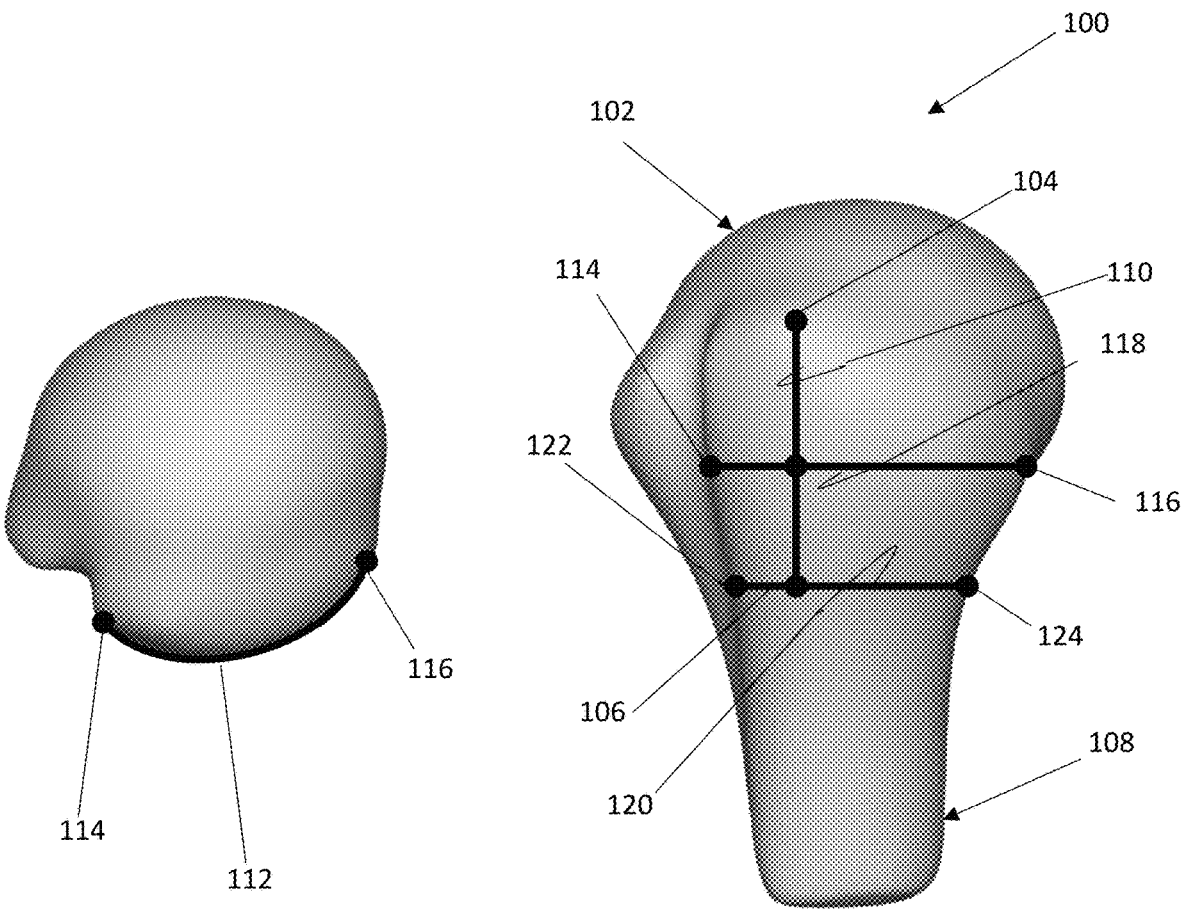
FIG. 4 is a perspective view of various anatomical parameters of a greater tuberosity of a proximal humerus bone analyzed in the development of the size and shape of the various embodiments of bone plate devices constructed in accordance with the present disclosure.

The size and shape of the head region 12 of the bone plate device 10 was designed based on an analysis of various anatomical parameters of a greater tuberosity of a proximal humerus bone. As shown in FIG. 4, the greater tuberosity 102 of the proximal humerus bone 100 to which the bone plate device 10 is to be attached is analyzed to determine several data points, including one or more of the data points described herein below. The first is a greater tuberosity top point 104, defined as a highest anatomical site on the upper curved edge of the greater tuberosity 102. The second is a greater tuberosity/shaft connection point 106, which is defined as the lower anatomical site on the greater tuberosity 102 that occurs at the site where the greater tuberosity 102 connects to the shaft 108 of the proximal humerus bone 100. Third, the greater tuberosity/shaft connection point 106 should be measured at a linear position compared to the greater tuberosity top point 104, so that a height 110 of the greater tuberosity 102 can be calculated. Fourth, the greater tuberosity 102 also possesses a curve 112 along the widest section thereof, and a radius of curvature of the curve 112 can be measured. Fifth, the linear distance can be measured from an anterior point 114 (referred to as "GT_max_ant_point") to a posterior point 116 (referred to as "GT_max_post_point"). The linear distance between the anterior and posterior points 114 and 116 provides a maximum width 118 of the greater tuberosity 102. Sixth, a minimum width 120 of the greater tuberosity 102 can be determined by measuring a linear distance between an anterior point 122 and a posterior point 124 through which the greater tuberosity/shaft connection point 106 linearly extends.

Lastly, a ratio of the maximum width 118 to the height 110 of the greater tuberosity 102 can be calculated.

Thus, the size and shape of the head region 12 of the bone plate device 10 is configured and adapted to substantially approximate these measurements, such that the head region 12 will lie substantially adjacent a majority of the surface of the greater tuberosity 102 and ensure adequate plate fit and sufficient treatment and healing. In addition, the minimum width 120 can be utilized in determining a width 50 of the shaft region 14 of the bone plate device 10.

It should be understood that the bone plate devices depicted in the figures of the subject application are depicted as left bone plate devices for purposes of consistency and illustration only. Right bone plate devices fully fall within the scope of the present disclosure and would be constructed exactly as described herein, except as mirrored versions of the left bone plate devices depicted in the figures.

EXAMPLES

Examples are provided hereinbelow. However, the present disclosure is to be understood to not be limited in its application to the specific experimentation, results, and laboratory procedures disclosed herein after. Rather, the Examples are simply provided as one of various embodiments and are meant to be exemplary, not exhaustive.

Example 1

This Example describes the analysis of various anatomical landmark parameters in the development of the bone plate devices of the present disclosure. A database of humerus bone CT scans was collected (from approximately 570 different patients). These CT scans were converted to 3D models, and anatomical parameters of interest were measured.

Figure 5:
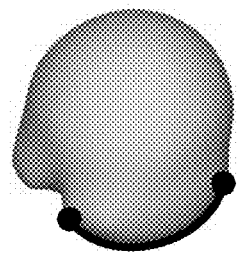
FIG. 5 graphically illustrates analysis of various proximal humeral anatomical parameters in development of the bone plate devices constructed in accordance with the present disclosure.
Figure 5:
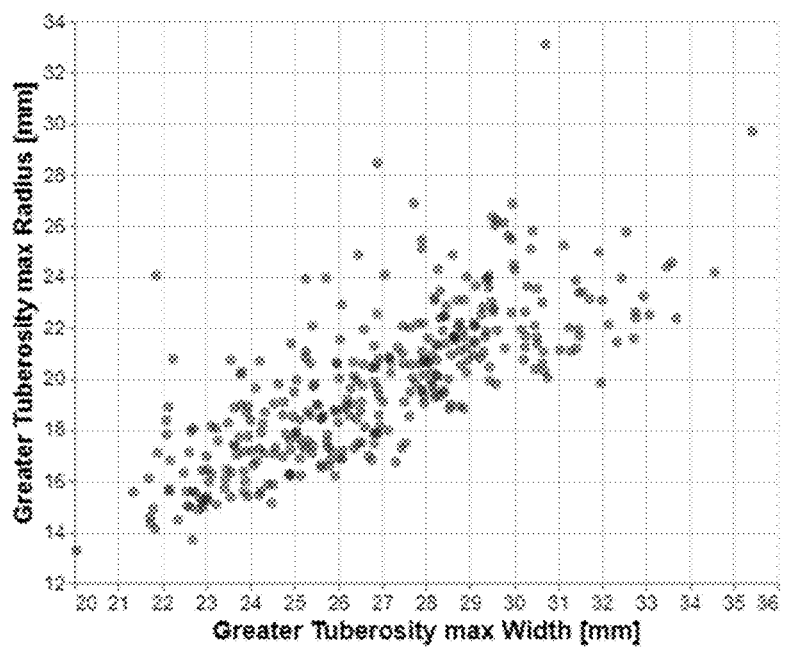
Figure 5:
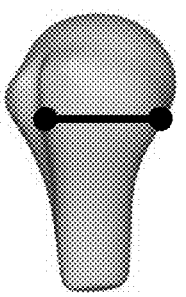

FIG. 5 graphically illustrates analysis of various anatomical parameters in development of the bone plate devices. In particular, the maximum width of the greater tuberosity is compared to the maximum radius of curvature of the greater tuberosity across a patient population. The maximum widths ranged from 17.82-35.43 mm (5-95%, 22-32 mm), while the maximum radii ranged from 13.27-33.34 mm (5-95%, 15-25 mm). Based on this Figure, it can be seen that these two values are directly proportional to one another as bone size increases. Thus, it was determined that "GT max width" is a primary variable that can be utilized to determine the size and shape of the head region of the bone plate devices to be used in accordance with the present disclosure.

Figure 6:
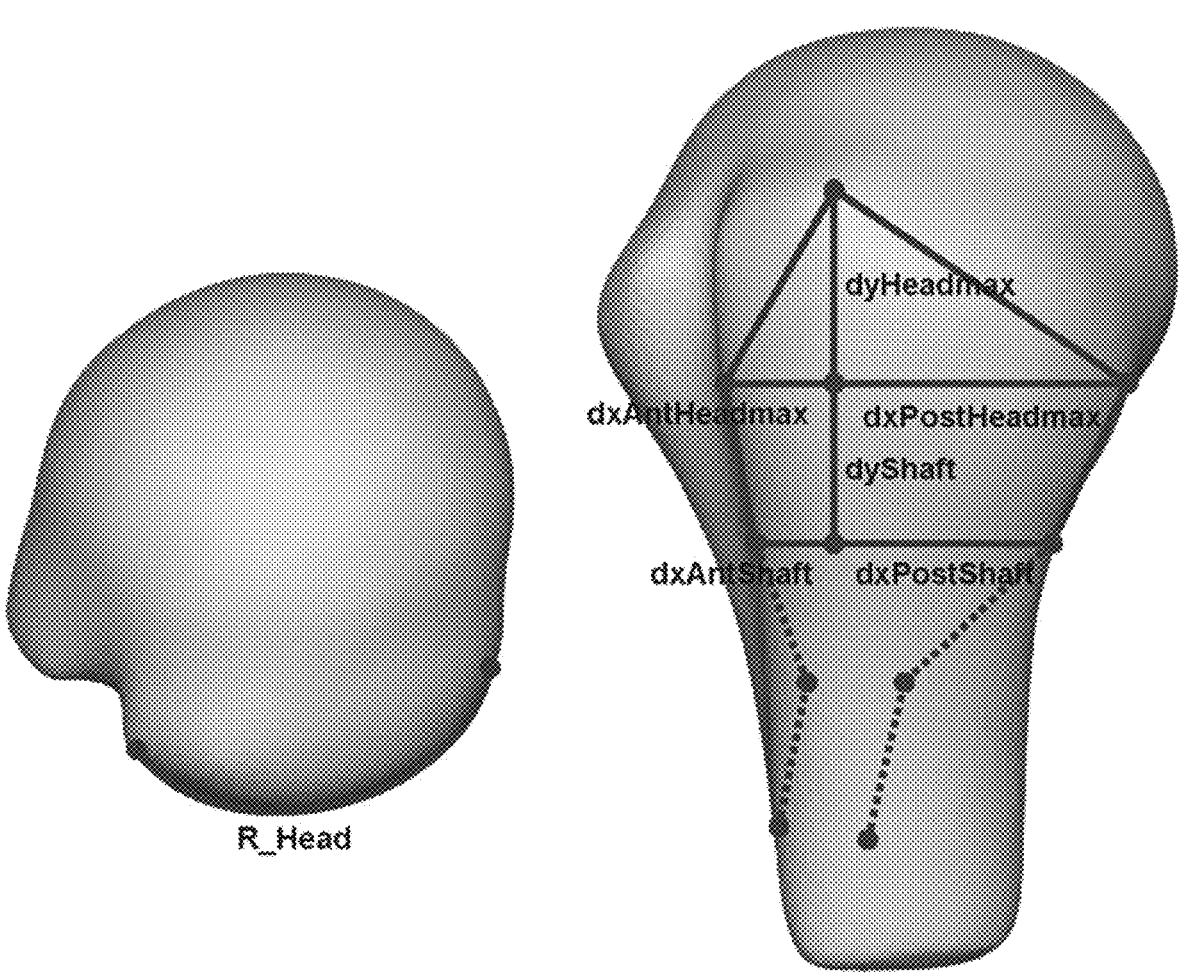
FIG. 6 is a perspective view illustrating that plate parameters of the system are determined based on statistical analysis of anatomical parameters.
Figure 7:
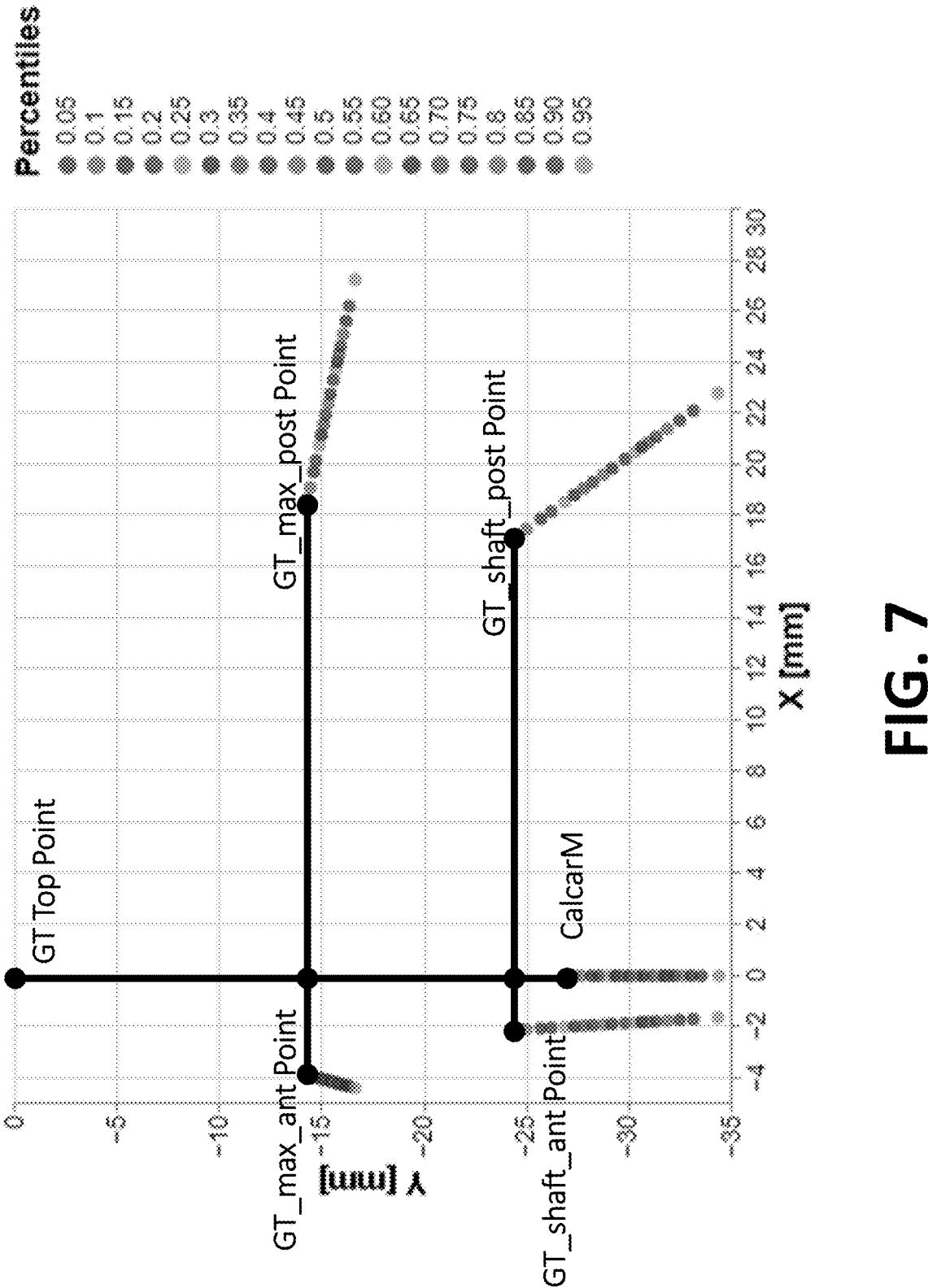
FIG. 7 graphically illustrates the anatomical landmark analysis by bone population percentiles.

Next, as shown in FIGS. 6-7, the morphological data points of a greater tuberosity top point, a greater tuberosity/shaft connection point, a greater tuberosity maximum anterior point, a greater tuberosity maximum posterior point, a greater tuberosity/shaft connection anterior point, and a greater tuberosity/shaft connection posterior point were determined across the patient population. Based on these data points, the maximum height ("dyHeadmax"), the maximum width ("dxHeadmax"), and the minimum width ("dyShaft") were also calculated across the patient population (FIG. 6). FIG. 7 illustrates the anatomical landmark analysis by bone population percentiles.

Figure 8:
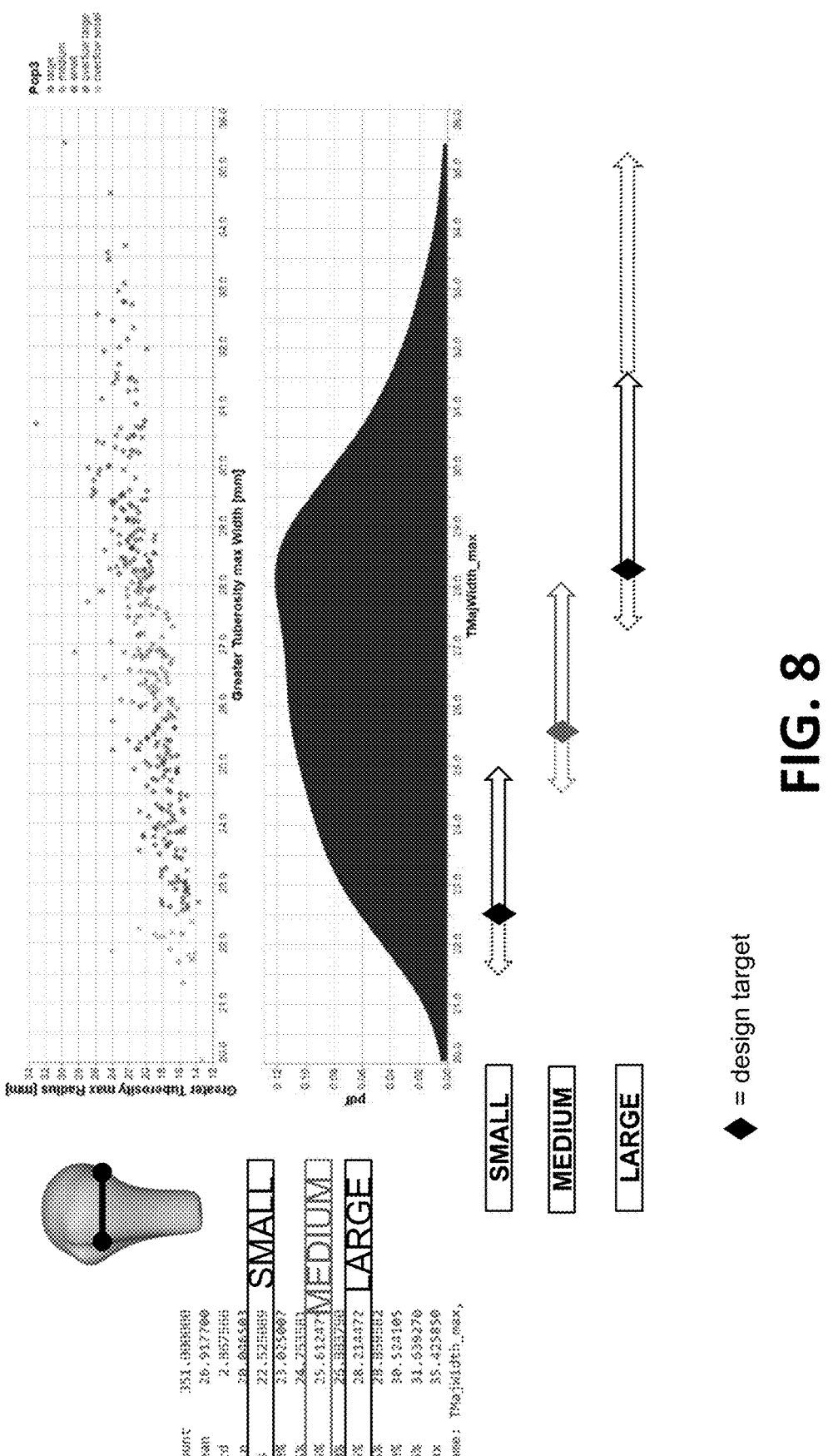
FIG. 8 graphically illustrates that patient population is stratified based on the main parameter of greater tuberosity max width versus max radius, and that design of various bone plate devices in accordance with the present disclosure is based on anatomical parameters within patient sub-populations.

Next, the patient population was stratified based on the main parameter of greater tuberosity maximum radius versus maximum width. As shown in FIG. 8, the patient population was divided into three sub-populations ("small," "medium," and "large"). Based on these sub-populations, three different sizes of bone plate devices were designed based on these anatomical parameters within patient sub-populations. In one non-limiting embodiment, these three different sizes of bone plate devices were designed with head region maximum widths of about 22.5 mm, about 25.6 mm, and about 28.2 mm, for the small, medium, and large devices, respectively. In another non-limiting embodiment, these three different sizes of bone plate devices were designed with head region maximum widths of about 22.5 mm, about 26.0 mm, and about 28.9 mm, for the small, medium, and large devices, respectively.

Figure 9:
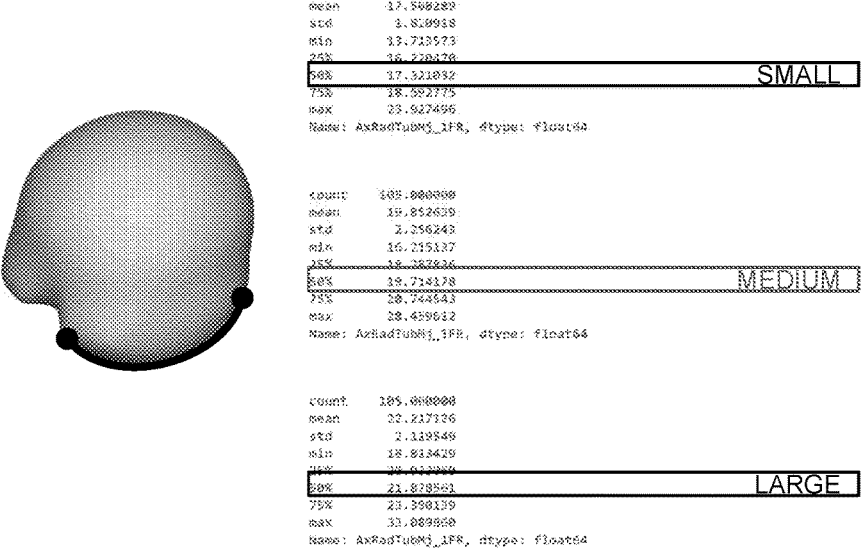
FIG. 9 graphically illustrates that secondary plate parameters are based on anatomical parameters within sub-populations.
Figure 9:
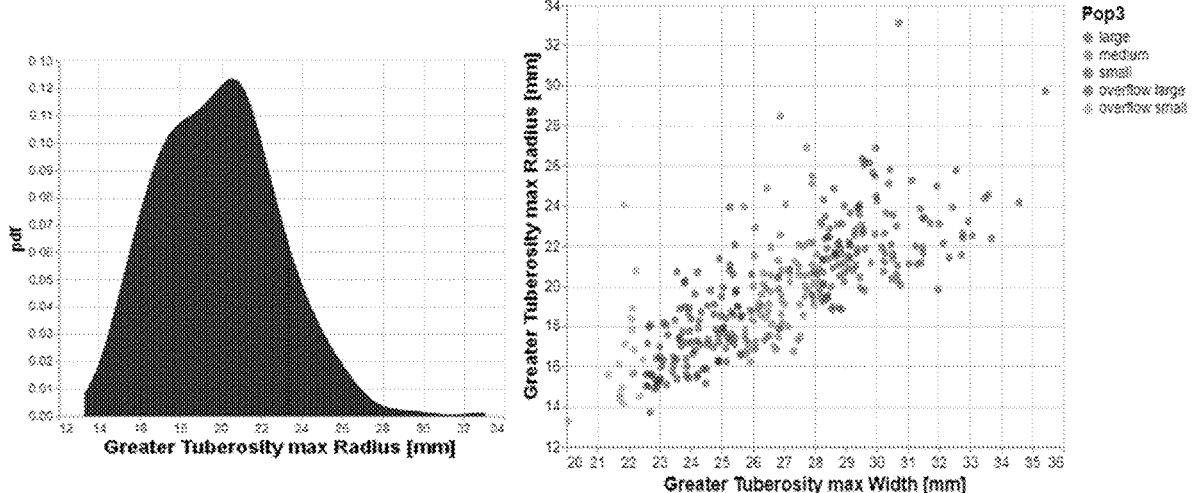

Next, the patient population was stratified based on greater tuberosity maximum width. As shown in FIG. 9, the patient population was divided into three sub-populations ("small," "medium," and "large"). Based on these sub-populations, three different shapes of bone plate devices were designed based on these anatomical parameters within patient sub-populations. The radius for the plate was determined by calculating the 50th percentile of the greater tuberosity maximum radius for each sub-population. In one non-limiting embodiment, the three different sizes of bone plate devices were designed with head region maximum radii of about 17.3 mm, about 19.7 mm, and about 21.9 mm, for the small, medium, and large devices, respectively. In another non-limiting embodiment, the three different sizes of bone plate devices were designed with head region maximum radii of about 17.4 mm, about 20.4 mm, and about 22.1 mm, for the small, medium, and large devices, respectively.

Figure 10:
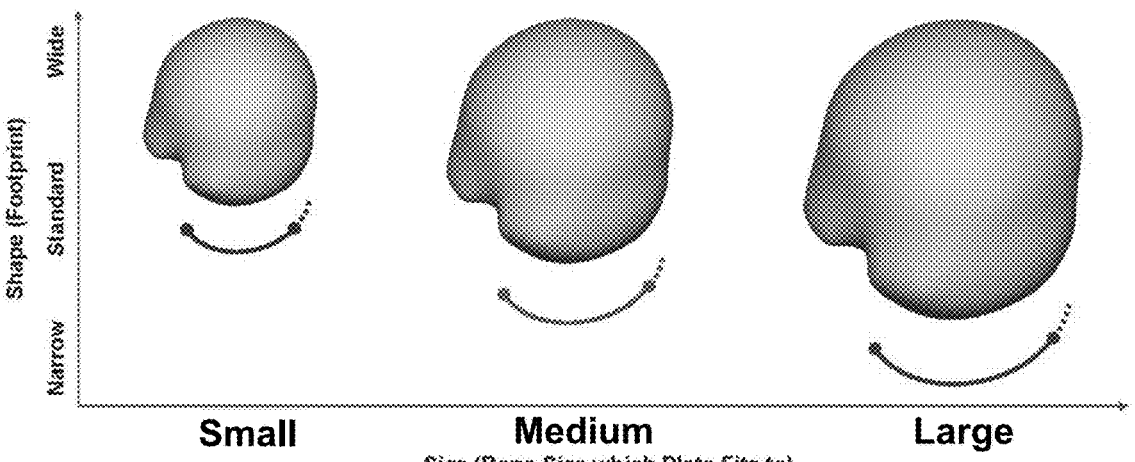
FIG. 10 illustrates the greater tuberosities of the three bone sizes to which one non-limiting embodiment of a system constructed in accordance with the present disclosure and containing three bone plate devices fit (i.e., small/medium/large populations).
Figure 11:
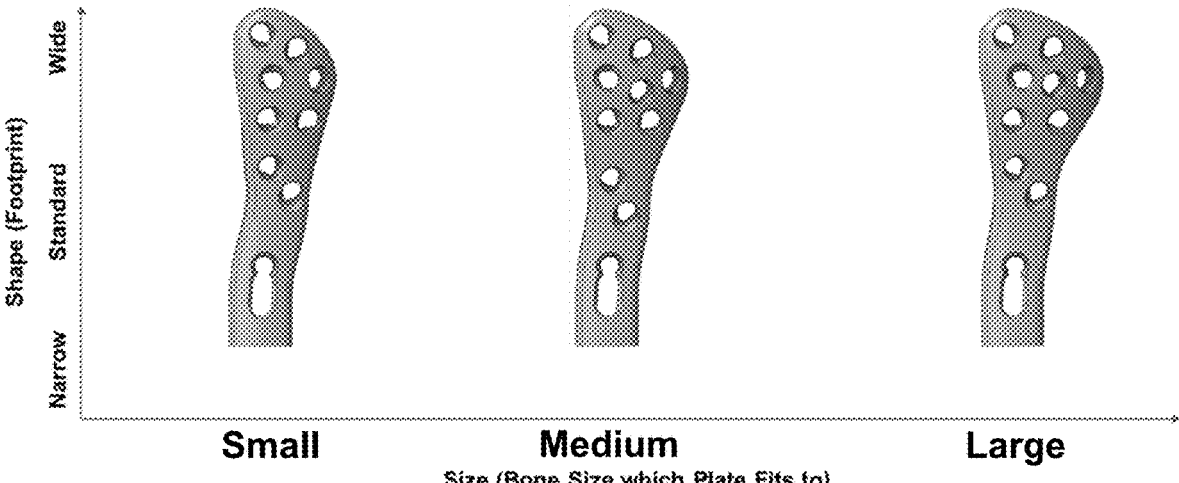
FIG. 11 contains perspective partial views of one non-limiting embodiment of a proximal humerus osteosynthesis system constructed in accordance with the present disclosure and comprising three bone plate devices (one each of small, medium, and large size). Note that screw hole positions and angulations are for purposes of illustration only and not to be construed as limiting.

FIGS. 10-11 illustrate the production of the system and kit of bone plate devices that include small, medium, and large devices based on the above analysis. FIG. 10 illustrates the greater tuberosities of the three bone sizes to which the three bone plate devices fit. FIG. 11 illustrates the head regions of the three bone plate devices (one each of small, medium, and large size). Note that size and shape of the head regions of the three bone plate devices differ from one another. In addition, the fastener hole positions and angulations depicted in FIG. 11 are for purposes of illustration only and should not be construed as limiting. Indeed, the numbers and patterns of fastener holes may vary between the small, medium, and large head regions.

Figure 12:
FIG. 12 contains perspective views of other non-limiting embodiments of a proximal humerus osteosynthesis system constructed in accordance with the present disclosure and comprising multiple bone plates for each of the small, medium, and large sizes.
Figure 12:
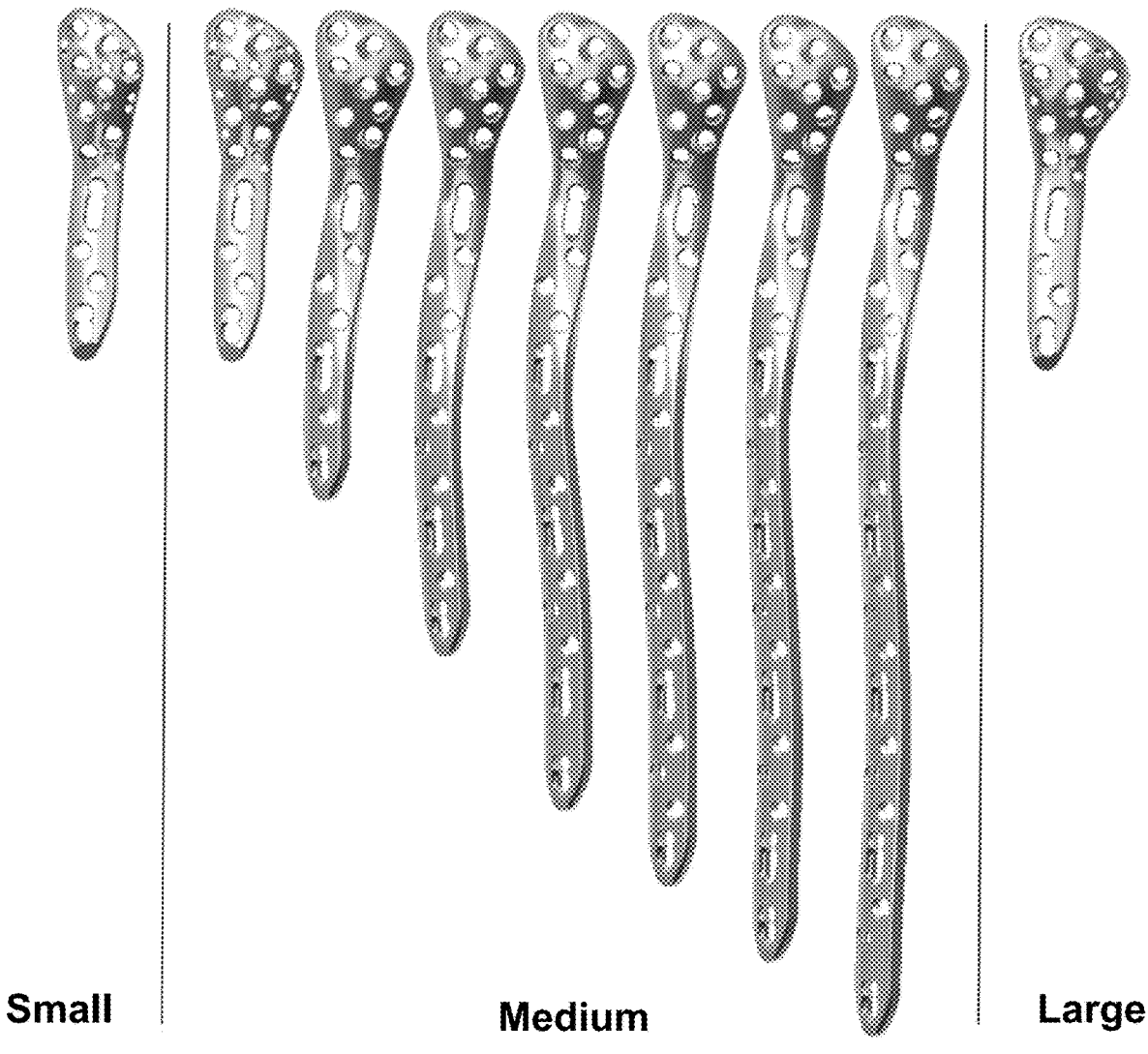
Figure 12:
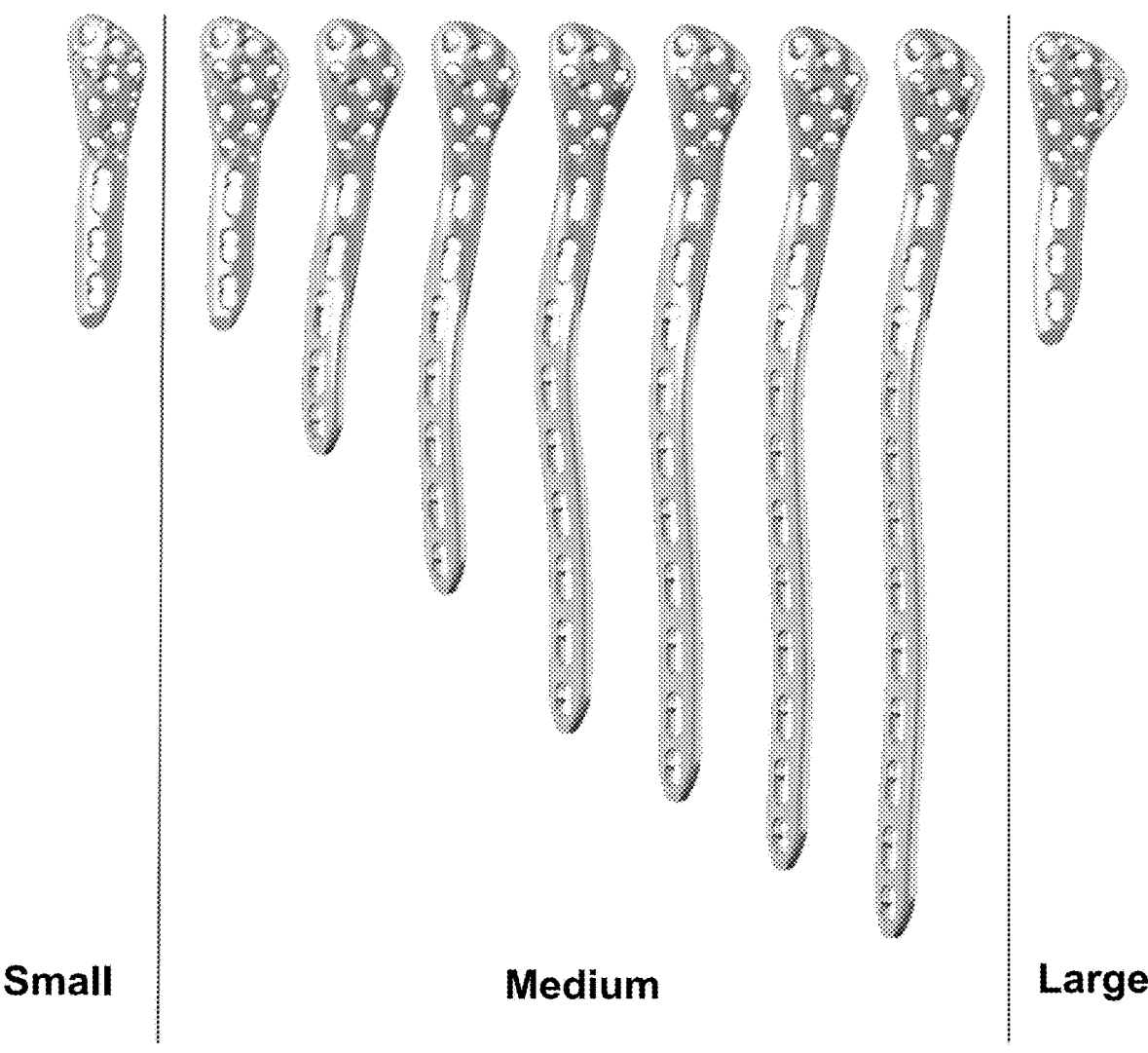

While FIG. 11 illustrates a single bone plate device for each small, medium, and large size, it will be understood that the system and kit may contain a plurality of each size of bone plate devices. For example (but not by way of limitation), FIG. 12 depicts a system/kit that includes multiple bone plate devices for one or more of the small, medium, and large sizes. For example (but not by way of limitation), Panel A of FIG. 12 contains a system/kit with two small, five medium, and two large bone plate devices, while Panels B and C of FIG. 12 contain a system/kit with one small, seven medium, and one large bone plate devices. In this manner, the bone plate devices in each of the small, medium, and large sizes have identical head regions but may differ from each other in other aspects, such as (but not limited to), the size of the shaft region, the length of the shaft region, the number of fastener hole(s) in the shaft region, the type of fastener hole(s) in the shaft region (i.e., single holes versus combination holes (i.e., combi-holes)), and/or the pattern of fastener hole(s) in the shaft region.

Also, note that the systems/kits of Panels B and C of FIG. 12 differ from one another in the numbers of fastener hole(s) in the shaft region, the types of fastener hole(s) in the shaft region, and the patterns of fastener hole(s) in the shaft region. In particular, each of the shafts of the devices in Panel C contains combi-holes that extend generally linearly down a length of the shaft, whereas each of the shafts of the devices in Panel B contains a combination of single holes and combi-holes that extend across a width of the shaft in various patterns. These configurations, however, are solely for purpose of illustration of the differences and degrees of complexity that the fastener holes can assume on the shafts of the devices. The devices of the systems/kits of the present disclosure can be provided with any configurations of fastener holes that allow the devices to function in accordance with the present disclosure.

Each of the systems/kits depicted in FIG. 12 contains the greatest number of bone plate devices in a medium head region size, and this plurality of medium bone plate devices is depicted as having a greater variation in shaft region lengths than the small and large head region size devices, including longer shaft region lengths than those provided in the small and large head region size. This distribution may be utilized because the medium head region size can be utilized with a larger percentage of the patient population. Also, the longer shaft region lengths are generally utilized with breaks that are present in the shaft of the humerus and thus are secured to the shaft at positions more distal to the head region of the bone plate device; as such, the fit of the head region against the greater tuberosity need not be quite as close as when a bone plate device having a shorter shaft region is utilized, and therefore can be utilized with a greater portion of the population.

However, this distribution of shaft region lengths between the three head region sizes should not be regarded as limiting; it will be understood that longer shaft region lengths may be present for any of the head region sizes in the system/kit.

Also, it will be understood that the depiction of a system/kit containing nine devices is for purposes of illustration only. Any number of devices (including any number of each size of devices) may be present in the systems/kits of the present disclosure.

In addition, while the figures depict left bone plate devices only, it will be understood that the systems/kits of the present disclosure will include both left and right bone plate devices that are simply mirrored versions of one another.

Example 2

While Example 1 described the development of a system/kit that contains three different sizes of bone plate devices (i.e., small, medium, and large devices), it will be understood that the system/kit may contain two sizes of devices or more than three sizes of devices. For example (but not by way of limitation), FIGS. 13-14 describe the development of two additional non-limiting embodiments of bone plate device systems and kits constructed in accordance with the present disclosure, wherein the systems/kits contain two different bone plate head sizes (i.e., small and large devices, based on stratification of the patient population into simply small and large sections).

Figure 13:
FIG. 13 illustrates the greater tuberosities of two bone sizes to which another non-limiting embodiment of a system constructed in accordance with the present disclosure and containing two bone plate devices fit (i.e., small and large populations).
Figure 14:
FIG. 14 illustrates the greater tuberosities of two bone sizes to which yet another non-limiting embodiment of a system constructed in accordance with the present disclosure and containing two bone plate devices fit (i.e., small and large populations) and two plate shapes (i.e., narrow and wide shapes) per plate device fit.

FIG. 13-14 illustrate the greater tuberosities of small and large bone size populations to which two different systems containing bone plate devices with small and large head regions are designed. Each of these figures depicts four plates: narrow small, wide small, narrow large, and wide large. Note that the "narrow" bone plate devices of FIG. 14 have a narrower footprint than the bone plate devices of FIG. 13, whereas the "wide" bone plate devices of FIG. 14 have a larger footprint than the bone plate devices of FIG. 13. The footprints of the devices can be varied, depending upon various reasons, such as (but not limited to) the location of the fracture, whether or not there is a need to cover the entire greater tuberosity, and/or other specific indications (i.e., simple fracture patterns require smaller plate footprints, whereas more complex fracture patterns require larger plate footprints).

Example 3

Figure 15:
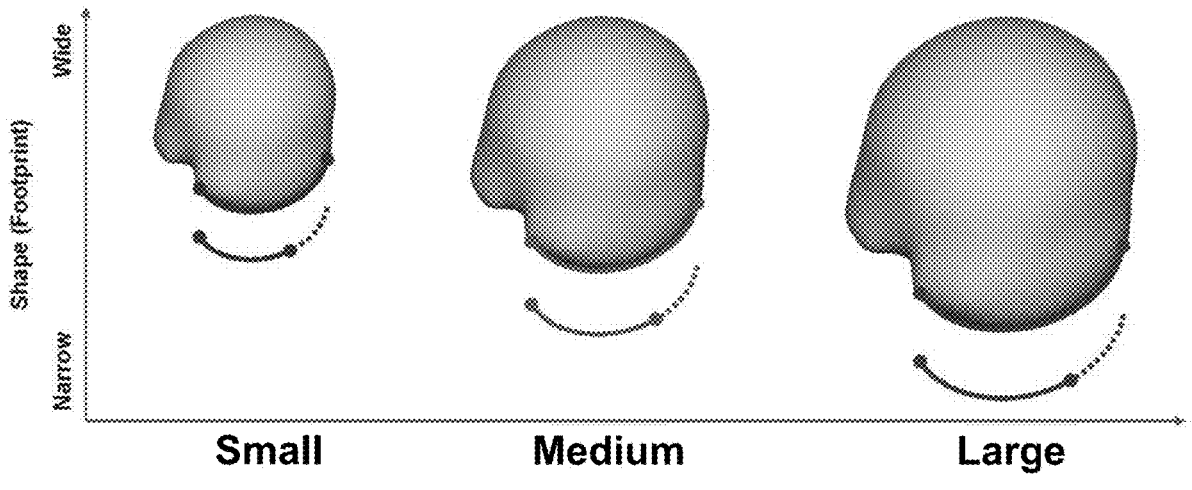
FIG. 15 illustrates the greater tuberosities of three bone sizes to which yet another non-limiting embodiment of a system constructed in accordance with the present disclosure and containing three bone plate devices fit (i.e., small, medium, and large populations) and two plate shapes (i.e., narrow and wide shapes) per plate device fit. Note that the narrow bone plate devices of FIG. 15 have a narrower footprint than the bone plate devices of FIG. 10.

FIG. 15 illustrates the development of yet another non-limiting embodiment of a bone plate device system and kit constructed in accordance with the present disclosure, wherein the system/kit contains three different bone plate head region sizes that fit to three different sections of the population (small, medium, and large populations). This system/kit differs from the system/kit of Example 1 and depicted in FIG. 10 by including six plates, which include wide and narrow footprints for each size. The footprints of the devices can be varied, depending upon various reasons, such as (but not limited to) the location of the fracture, whether or not there is a need to cover the entire greater tuberosity, and/or other specific indications (i.e., simple fracture patterns require smaller plate footprints, whereas more complex fracture patterns require larger plate footprints).

Example 4

Figure 16:
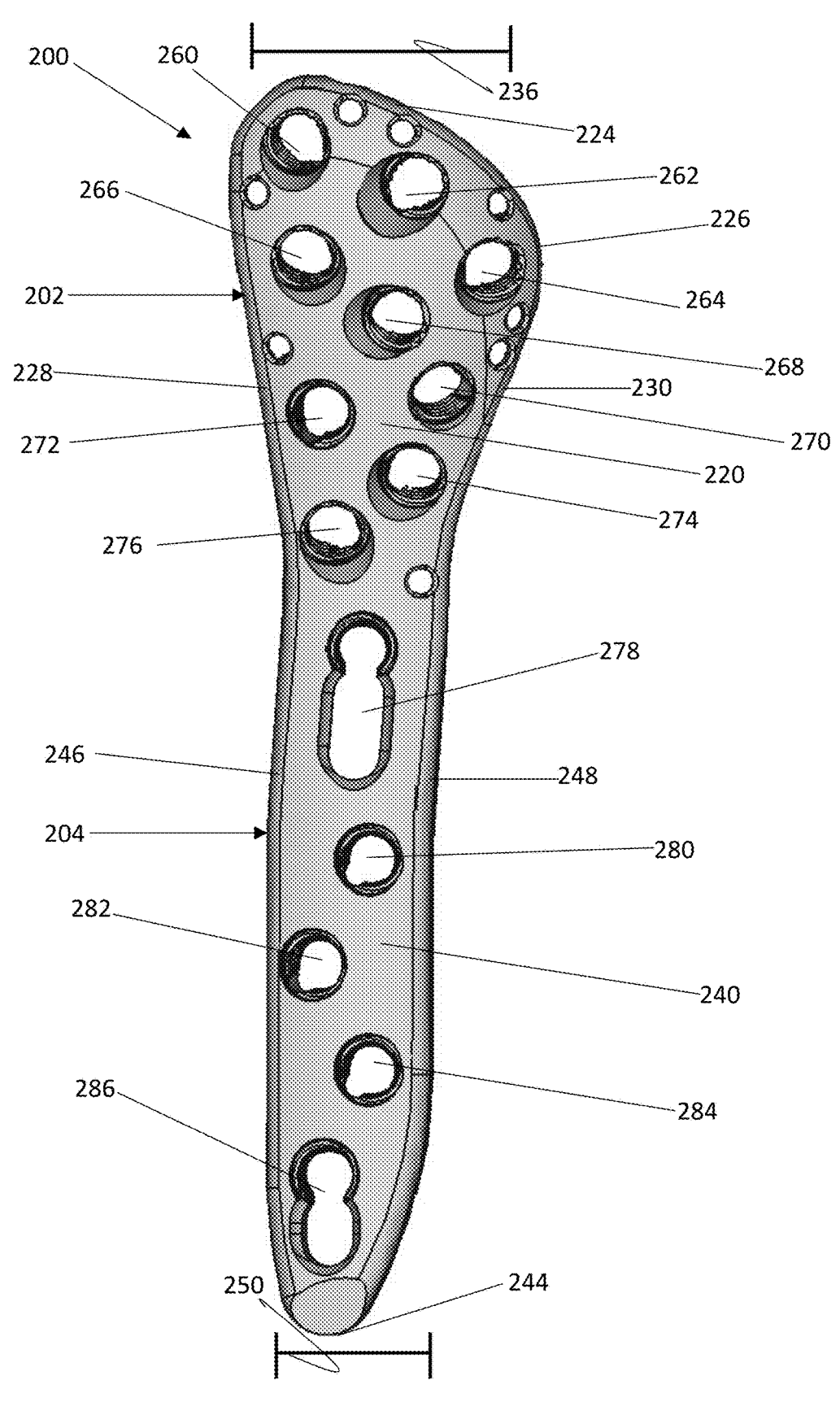
FIG. 16 is a perspective view of another non-limiting embodiment of a proximal humerus bone plate device constructed in accordance with the present disclosure.
Figure 17:
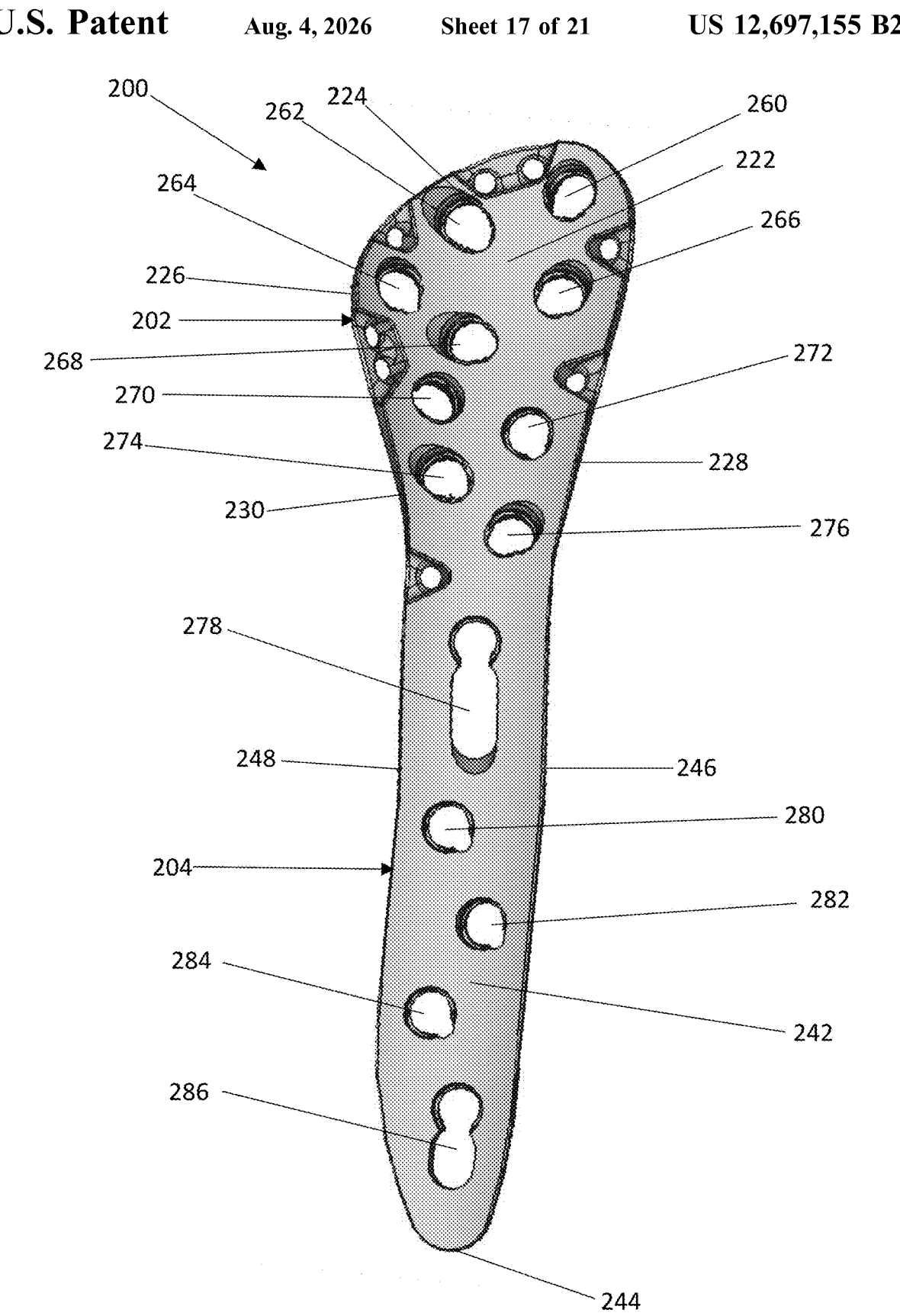
FIG. 17 is a perspective view from the bone-facing surface of the bone plate device of FIG. 16.
Figure 18:
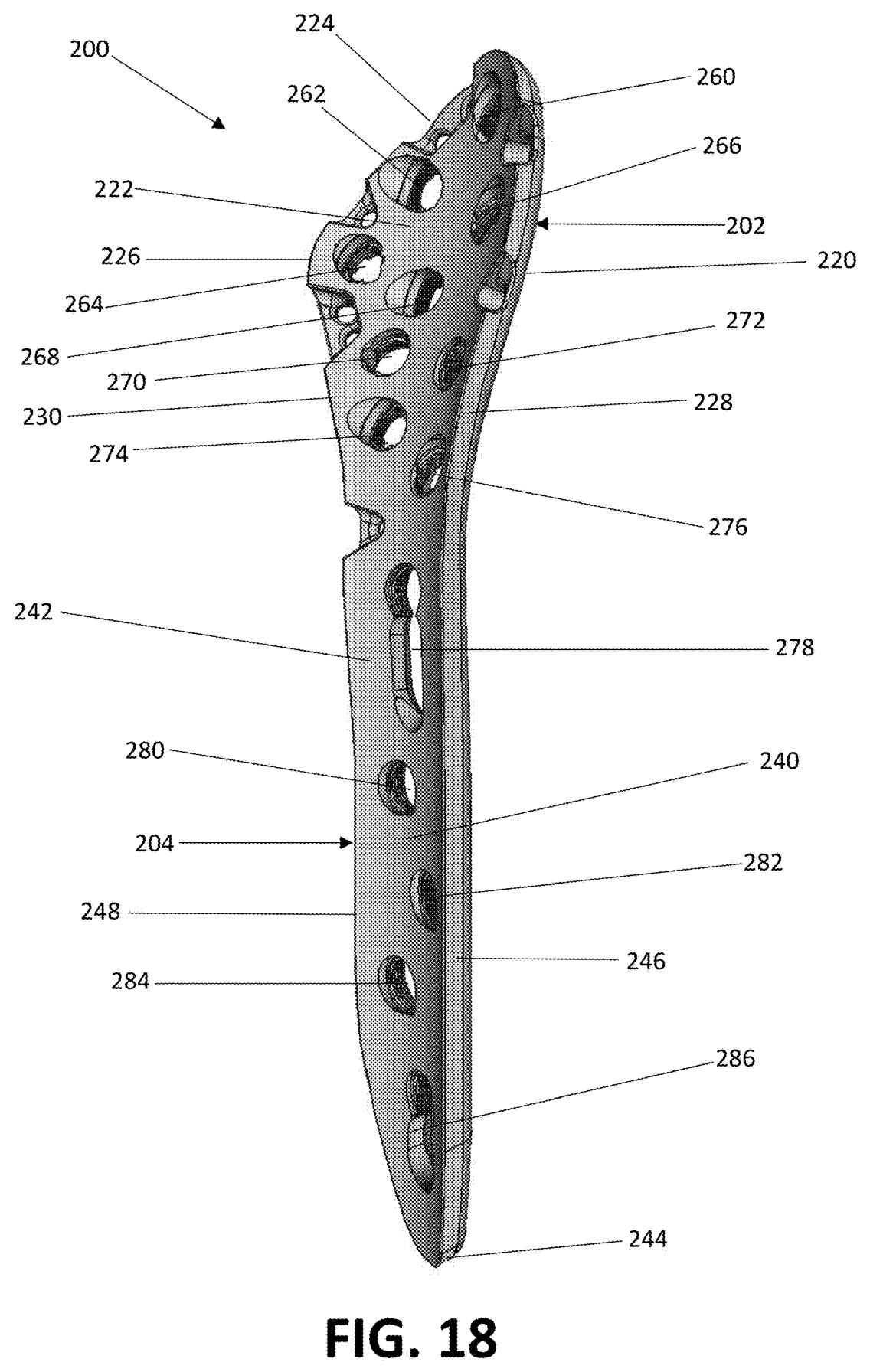
Figure 19:
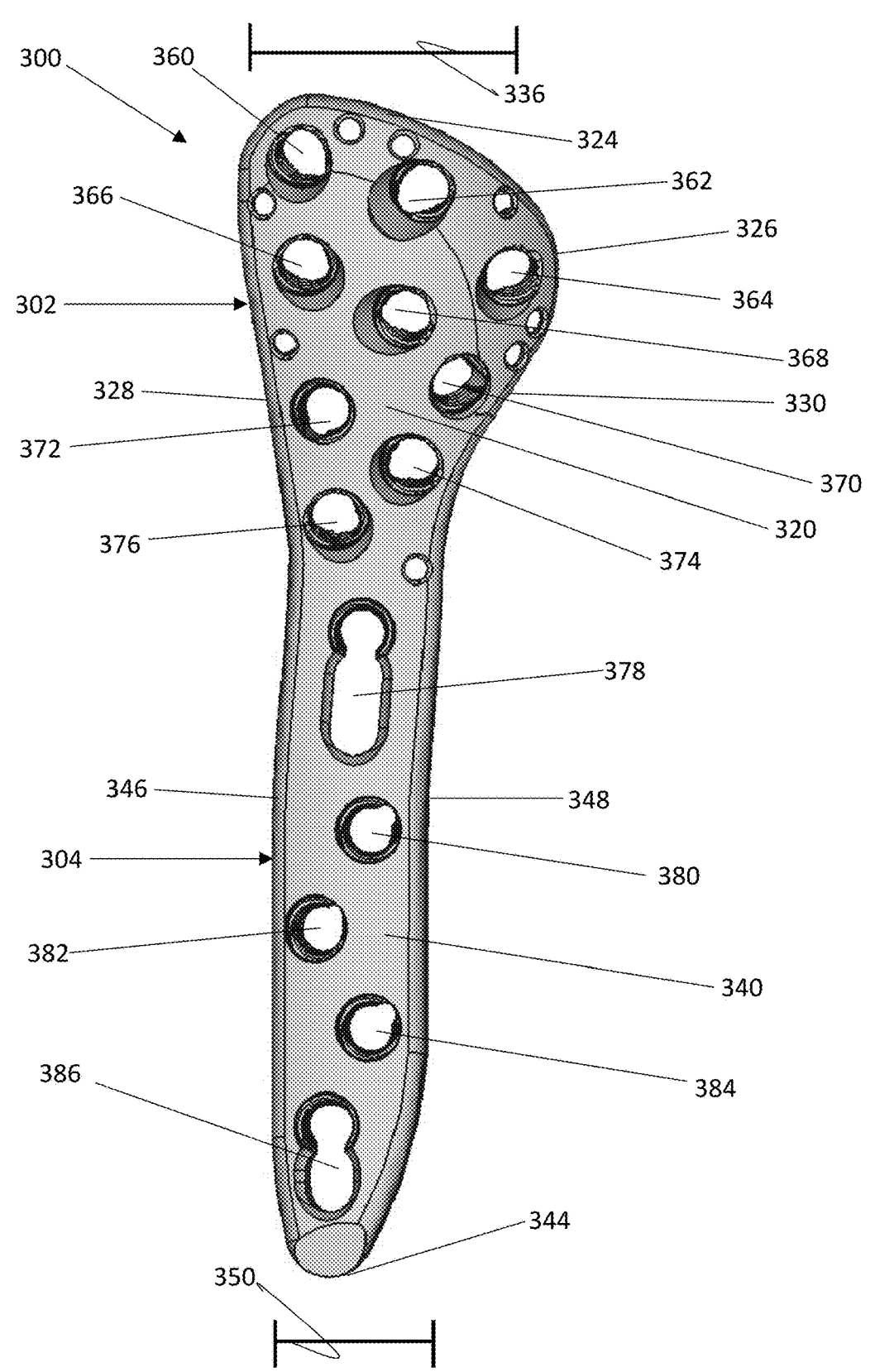
FIG. 19 is a perspective view of yet another non-limiting embodiment of a proximal humerus bone plate device constructed in accordance with the present disclosure.
Figure 20:
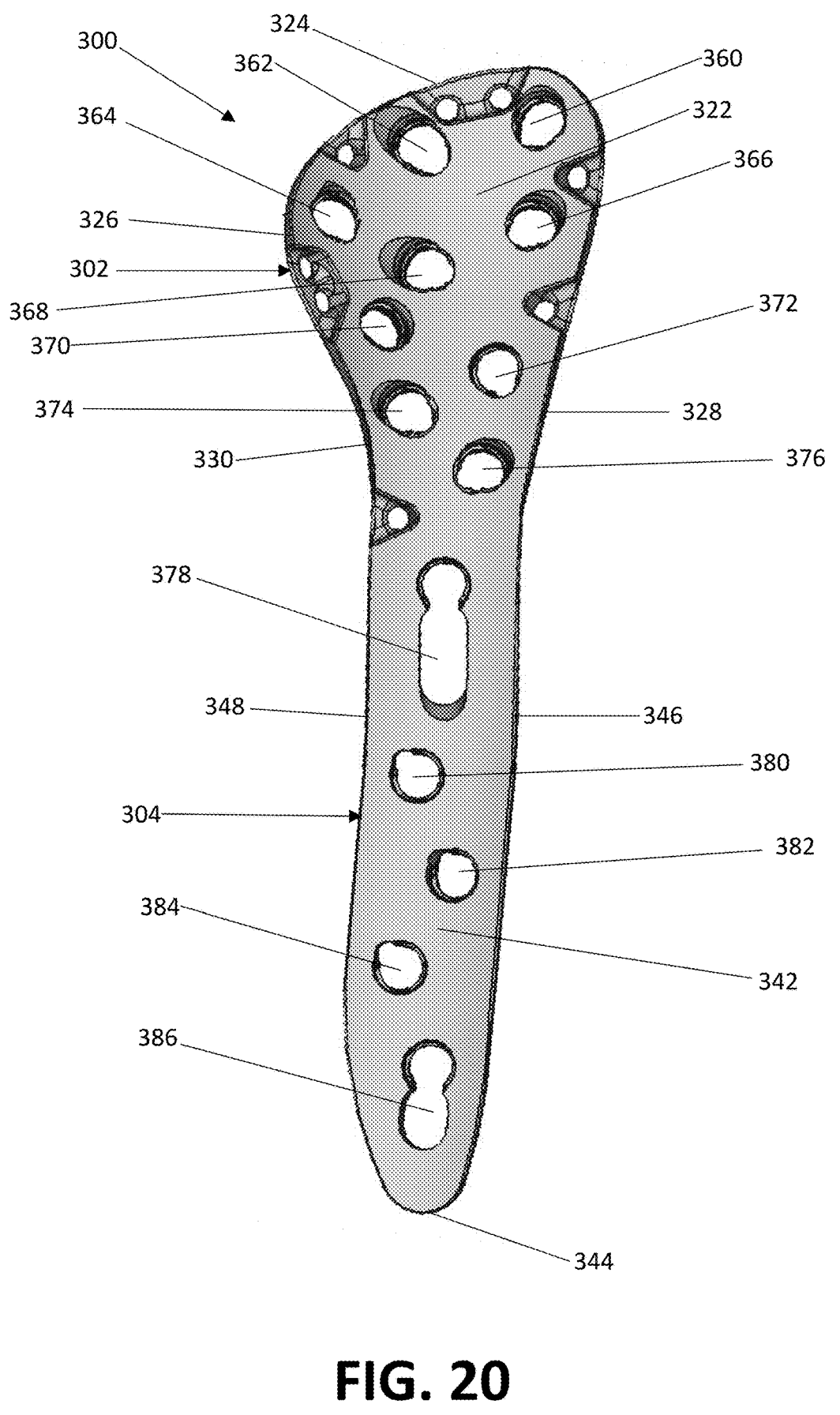
Figure 21:
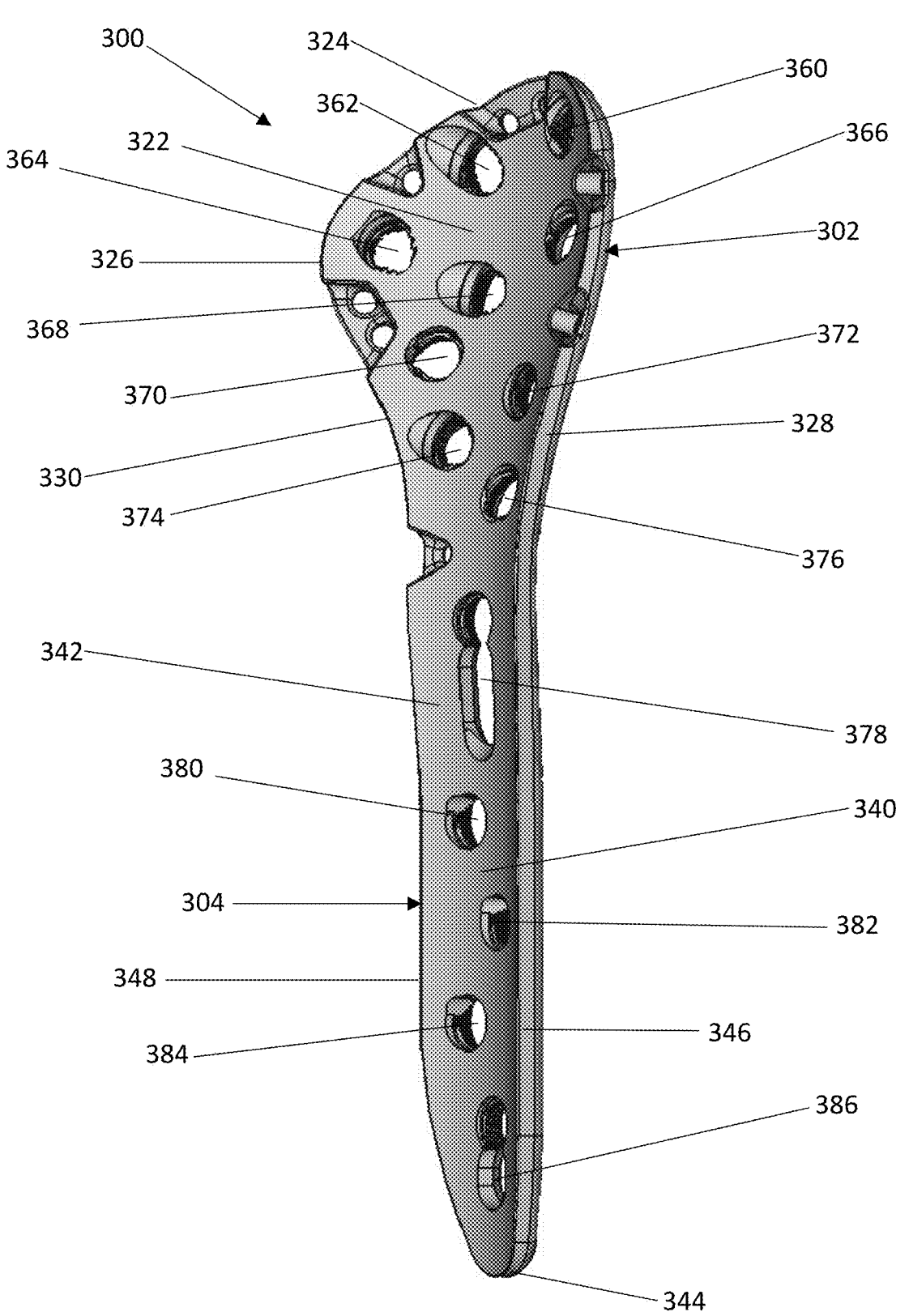
FIG. 21 is a perspective view from a side of the bone plate device of FIG. 19. In one non-limiting embodiment, the devices of FIGS. 1-2 and 16-21 form a system or kit in which (for example, but not by way of limitation), the bone plate device of FIGS. 1-2 is a "small" size, the bone plate device of FIGS. 16-18 is a "medium" size, and the bone plate device of FIGS. 19-21 is a "large" size.

This Example describes the structures of another non-limiting embodiment of a bone plate device system and kit constructed in accordance with the present disclosure, wherein the system/kit contains three different bone plate head sizes. In this system/kit, the "small" head region size bone plate device is shown in FIGS. 1-3. FIGS. 16-18 depict the "medium" head region size bone plate device, while FIGS. 19-21 depict the "large" head region size bone plate device.

FIGS. 16-18 depict a proximal humeral bone plate device 200 constructed in accordance with the present disclosure. The bone plate device 200 comprises a head region 202 and a shaft region 204. The head region 202 is configured to conform to and adapted to be attached to a greater tuberosity of the proximal humerus, while the shaft region 204 is configured and adapted to be attached to a shaft of the humerus.

The head region 202 extends at a lateral angle X relative to a longitudinal axis Y (as depicted in FIG. 1) and has an upper surface 220, an opposed bone-facing surface 222, an upper boundary edge 224 with a curvature and a lower end 226, a first side edge 228, and a second side edge 230, wherein each of the first and second side edges 228 and 230 extends from the upper boundary edge 224 (for example, but not by way of limitation, FIG. 16 illustrates the second side edge 230 as extending from the lower end 226 of the upper boundary edge 224). The curved bone-facing surface 222 with a radius of curvature 234 that approximately conforms to a shape of a greater tuberosity of a proximal humerus. The head region 202 also has a maximum width 236 extending between the lower end 226 of the upper boundary edge 224 and the opposing side edge (in this case, the first side edge 228).

The shaft region 204 comprises an elongated portion extending along the longitudinal axis Y and has an upper surface 240 (that is contiguous with the upper surface 220 of the head region 202), an opposed bone-facing surface 242 (that is contiguous with the bone-facing surface 222 of the head region 202), a lower edge 244, a first side edge 246 (that is contiguous with the first side edge 228 of the head region 202), a second side edge 248 (that is contiguous with the second side edge 230 of the head region 202), and a width 250 extending between the first and second side edges 246 and 248.

In addition, each of the head and shaft regions 202 and 204 has at least one fastener hole extending through the upper and lower surfaces thereof; each of the fastener holes is configured for receiving a bone fastener (such as, but not limited to, a screw, pin, rod, nail, or other type of fixation device) for securing the bone plate device 200 to the humerus. For example (but not by way of limitation), the head region 202 is depicted as having fastener holes 260, 262, 264, 266, 268, 270, 272, 274, and 276 extending through the upper surface 220 and bone-facing surface 224 of the head region 202 for receiving bone fasteners for securing the head region 202 to the greater tuberosity such that the upper edge curvature of the head region is disposed substantially adjacent an upper curvature of the greater tuberosity. The fastener holes 260, 262, and 264 are depicted as being generally disposed in a row along the lateral angle X so as to generally follow the curvature of the upper boundary edge 224 of the head region 202. In addition (but not by way of limitation), the fastener holes 266, 268, and 270 are depicted as being generally disposed in a row along the lateral angle X and approximately along a mid-section of the head region 202, while the fastener holes 272 and 274 are depicted as also being generally disposed in a row along the lateral angle X and along a lower portion of the head region 202. However, this depiction of row patterns and disposal along a particular angle is for purposes of illustration only; it will be understood that any of the rows of fastener holes may assume any patterns and be disposed along a horizontal or longitudinal angle.

In addition, the shaft region 204 is depicted as having fastener holes 278, 280, 282, 284, and 286 extending through the upper surface 240 and bone-facing surface 242 of the shaft region 204 for receiving bone fasteners for securing the shaft region 204 of the bone plate device 200 to the shaft of the humerus. However, the number and pattern of fastener holes depicted in FIGS. 16-18 is for purposes of illustration only; it will be understood that the bone plate devices of the present disclosure can be provided with any number of fastener holes and any pattern of fastener holes that allow the bone plate devices to function in accordance with the present disclosure.

Also, one or more of the fastener holes may be provided with one or more features or structures that allow the fastener holes to interact with the bone fasteners and aid in securing the bone plate device 200 to the humerus. For example (but not by way of limitation), when one or more of the bone fasteners is a screw, the corresponding fastener hole may be provided with threading around the edges of the opening.

FIGS. 19-21 depict a proximal humeral bone plate device 300 constructed in accordance with the present disclosure. The bone plate device 300 comprises a head region 302 and a shaft region 304. The head region 302 is configured to conform to and adapted to be attached to a greater tuberosity of the proximal humerus, while the shaft region 304 is configured and adapted to be attached to a shaft of the humerus.

The head region 302 extends at a lateral angle X relative to a longitudinal axis Y (as depicted in FIG. 1) and has an upper surface 320, an opposed bone-facing surface 322, an upper boundary edge 324 with a curvature and a lower end 326, a first side edge 328, and a second side edge 330, wherein each of the first and second side edges 328 and 330 extends from the upper boundary edge 324 (for example, but not by way of limitation, FIG. 19 illustrates the second side edge 330 as extending from the lower end 326 of the upper boundary edge 324). The head region 302 has a curved bone-facing surface 332 with a radius of curvature 334 that approximately conforms to a shape of a greater tuberosity of a proximal humerus. The head region 302 also has a maximum width 336 extending between the lower end 326 of the upper boundary edge 324 and the opposing side edge (in this case, the first side edge 328).

The shaft region 304 comprises an elongated portion extending along the longitudinal axis Y and has an upper surface 340 (that is contiguous with the upper surface 320 of the head region 302), an opposed bone-facing surface 342 (that is contiguous with the bone-facing surface 322 of the head region 302), a lower edge 344, a first side edge 346 (that is contiguous with the first side edge 328 of the head region 302), a second side edge 348 (that is contiguous with the second side edge 330 of the head region 302), and a width 350 extending between the first and second side edges 346 and 348.

In addition, each of the head and shaft regions 302 and 304 has at least one fastener hole extending through the upper and lower surfaces thereof; each of the fastener holes is configured for receiving a bone fastener (such as, but not limited to, a screw, pin, rod, nail, or other type of fixation device) for securing the bone plate device 300 to the humerus. For example (but not by way of limitation), the head region 302 is depicted as having fastener holes 360, 362, 364, 366, 368, 370, 372, 374, and 376 extending through the upper surface 320 and bone-facing surface 324 of the head region 302 for receiving bone fasteners for securing the head region 302 to the greater tuberosity such that the upper edge curvature of the head region 302 is disposed substantially adjacent an upper curvature of the greater tuberosity. The fastener holes 360, 362, and 364 are depicted as being generally disposed in a row along the lateral angle X so as to generally follow the curvature of the upper boundary edge 324 of the head region 302. In addition (but not by way of limitation), the fastener holes 366, 368, and 370 are depicted as being generally disposed in a row along the lateral angle X and approximately along a mid-section of the head region 302, while the fastener holes 372 and 374 are depicted as also being generally disposed in a row along the lateral angle X and along a lower portion of the head region 302. However, this depiction of row patterns and disposal along a particular angle is for purposes of illustration only; it will be understood that any of the rows of fastener holes may assume any patterns and be disposed along a horizontal or longitudinal angle.

In addition, the shaft region 304 is depicted as having fastener holes 378, 380, 382, 384, and 386 extending through the upper surface 340 and bone-facing surface 342 of the shaft region 304 for receiving bone fasteners for securing the shaft region 304 of the bone plate device 300 to the shaft of the humerus. However, the number and pattern of fastener holes depicted in FIGS. 19-21 is for purposes of illustration only; it will be understood that the bone plate devices of the present disclosure can be provided with any number of fastener holes and any pattern of fastener holes that allow the bone plate devices to function in accordance with the present disclosure.

Also, one or more of the fastener holes may be provided with one or more features or structures that allow the fastener holes to interact with the bone fasteners and aid in securing the bone plate device 300 to the humerus. For example (but not by way of limitation), when one or more of the bone fasteners is a screw, the corresponding fastener hole may be provided with threading around the edges of the opening.

The bone plate devices 10, 200, and 300 of FIGS. 1-3, FIGS. 16-18, and FIGS. 19-21, respectively, differ from one another in the size and/or shapes of the head regions 12, 202, and 302, respectively, thereof. For example, in one non-limiting embodiment, the head regions 12, 202, and 302 may be provided with differing maximum widths of about 22.5 mm, about 25.6 mm, and about 28.2 mm, respectively, and/or the head regions 12, 202, and 302 may be provided with differing maximum radii of curvature of about 17.3 mm, about 19.7 mm, and about 21.9 mm, respectively, based on the morphological measurements obtained in Example 1. In another non-limiting embodiment, the head regions 12, 202, and 302 may be provided with differing maximum widths of about 22.5 mm, about 26.0 mm, and about 28.9 mm, respectively, and/or the head regions 12, 202, and 302 may be provided with differing maximum radii of curvature of about 17.4 mm, about 20.4 mm, and about 22.1 mm, respectively. However, the head regions 12, 202, and 302 all possess a ratio of maximum width to height in a range of from about 1.2:1 to about 1.5:1 (such as, for example, but not by way of limitation, a ratio of from about 1.25:1 to about 1.35:1, a ratio of from about 1.27:1 to about 1.33:1, a ratio of from about 1.28:1 to about 1.32:1, a ratio of from about 1.29:1 to about 1.31:1, etc.).

Non-Limiting Illustrative Embodiments

Illustrative embodiment 1. A bone plate device configured and adapted to be attached to a surface of a proximal humerus for promoting healing of a fracture in the humerus of a subject, the device comprising: a shaft region comprising an elongated portion extending along a longitudinal axis, the shaft region configured and adapted to be attached to a shaft of the humerus, the shaft region having an upper surface, an opposed bone-facing surface, a lower edge, a first side edge, a second side edge, and a width extending between the first and second side edges, and wherein the shaft region has at least one fastener hole extending through the upper surface and bone-facing surface for receiving at least one bone fastener for securing the shaft region of the bone plate device to the shaft of the humerus; and a head region configured to conform to and adapted to be attached to a greater tuberosity of the proximal humerus, the head region extending at a lateral angle relative to the longitudinal axis, the head region having an upper surface, an opposed bone-facing surface, an upper boundary edge with a curvature, a first side edge, and a second side edge, the head region having a curved bone-facing surface with a radius of curvature that approximately conforms to a shape of the greater tuberosity, wherein the head region has a maximum width extending between the first or second side edge and a lower end of the upper boundary edge, wherein the head region has a ratio of maximum width to height in a range of from about 1.2:1 to about 1.5:1, and wherein the head region comprises a plurality of fastener holes extending through the upper surface and bone-facing surface for receiving bone fasteners for securing the head region to the greater tuberosity such that the upper edge curvature of the head region is disposed substantially adjacent an upper curvature of the greater tuberosity.

Illustrative embodiment 1A. The device of Illustrative embodiment 1, wherein the head region has a ratio of maximum width to height in a range of from about 1.25:1 to about 1.35:1.

Illustrative embodiment 1B. The device of Illustrative embodiment 1 or 1A, wherein the head region has a ratio of maximum width to height in a range of from about 1.27:1 to about 1.33:1.

Illustrative embodiment 1C. The device of Illustrative embodiment 1, wherein the head region has a ratio of maximum width to height in a range of from about 1.3:1 to about 1.44:1.

Illustrative embodiment 1D. The device of any of Illustrative embodiments 1 or 1C, wherein the head region has a ratio of maximum width to height in a range of from about 1.38:1 to about 1.42:1.

Illustrative embodiment 2. The device of any of Illustrative embodiments 1-1D, wherein the size and configuration of the bone plate device is determined based on a plurality of morphological measurements of the greater tuberosity of the humerus, wherein the morphological measurements comprise a greater tuberosity top point, a greater tuberosity/shaft connection point, a greater tuberosity maximum anterior point, and a greater tuberosity maximum posterior point.

Illustrative embodiment 3. The device of Illustrative embodiment 2, wherein the height of the head region is calculated as a distance between the greater tuberosity top point and the greater tuberosity/shaft connection point, and wherein the maximum width is calculated as a distance between the greater tuberosity maximum anterior point and the greater tuberosity maximum posterior point.

Illustrative embodiment 4. The device of any of Illustrative embodiments 1-3, wherein the head region has a maximum width in a range of from about 22 mm to about 29 mm and a maximum radius of curvature in a range of from about 17 mm to about 23 mm.

Illustrative embodiment 5. The device of any of Illustrative embodiments 1-4, wherein the plurality of fastener holes in the head region has a pattern comprising an upper row of at least three holes, a middle row of at least two holes, and a lower row of at least two holes.

Illustrative embodiment 5A. The device of Illustrative embodiment 5, wherein the upper row comprises the at least three holes disposed along a first angled line.

Illustrative embodiment 5B. The device of Illustrative embodiment 5A, wherein the middle row comprises the at least two holes disposed along a second angled line.

Illustrative embodiment 5C. The device of Illustrative embodiment 5B, wherein the lower row comprises the at least two holes disposed along a third angled line.

Illustrative embodiment 5D. The device of Illustrative embodiment 5C, wherein the first, second, and third angled lines are substantially parallel.

Illustrative embodiment 5E. The device of any of Illustrative embodiments 5-5D, wherein the upper row is configured to be adjacent an upper $\frac{1}{4}$th to $\frac{1}{3}$rd of a humeral head, the middle row is configured to be adjacent a middle of the humeral head, and the lower row is configured to be adjacent a calcar.

Illustrative embodiment 5F. The device of any of Illustrative embodiments 5-5E, wherein the upper row comprises three holes, the middle row comprises 2-3 holes, and the lower row comprises 2-3 holes.

Illustrative embodiment 6. The device of any of Illustrative embodiments 5-5F, wherein at least one of the rows of holes is disposed along the lateral angle.

Illustrative embodiment 6A. The device of any of Illustrative embodiments 1-6, wherein at least one fastener hole in the shaft region comprises at least one combination hole.

Illustrative embodiment 6B. The device of Illustrative embodiment 6A, wherein the shaft region comprises a plurality of combination fastener holes.

Illustrative embodiment 6C. The device of Illustrative embodiment 6A or 6B, wherein the shaft region comprises between one (1) to twelve (12) combination fastener holes.

Illustrative embodiment 6D. The device of Illustrative embodiment 6C, wherein the plurality of combination fastener holes extends substantially linearly along the longitudinal axis of the shaft region.

Illustrative embodiment 6E. The device of any of Illustrative embodiments 1-6D, wherein the shaft region comprises at least one combination fastener hole and at least one single fastener hole.

Illustrative embodiment 6F. The device of Illustrative embodiment 6E, wherein the shaft region comprises a plurality of combination fastener holes and a plurality of single fastener holes.

Illustrative embodiment 6G. The device of Illustrative embodiment 6E or 6F, wherein the shaft region comprises from 1 to 20 combination fastener holes and from 1 to 20 single fastener holes.

Illustrative embodiment 7. A kit, comprising: at least a first bone plate device configured and adapted to be attached to a surface of a proximal humerus; and at least a second bone plate device configured and adapted to be attached to a surface of a proximal humerus; and wherein each of the first and second devices is a device of any of Illustrative embodiments 1-6G; and wherein at least the head regions of the first and second devices have different sizes and/or shapes.

Illustrative embodiment 7A. The kit of Illustrative embodiment 7, wherein the head region of the first bone plate device has a different radius of curvature than the head region of the second bone plate device.

Illustrative embodiment 8. The kit of Illustrative embodiment 7 or 7A, wherein a pattern of the plurality of fastener holes in the head region of the first device is different from a pattern of the plurality of fastener holes in the head region of the second device.

Illustrative embodiment 9. The kit of any of Illustrative embodiments 7-8, further comprising at least one third bone plate device configured and adapted to be attached to a surface of a proximal humerus, wherein the third device is a device of any one of claims 1-6E, and wherein at least the head region of the third device has a different size and/or shape than the first and second devices.

Illustrative embodiment 10. The kit of Illustrative embodiment 9, wherein a pattern of the plurality of fastener holes in the head region of the third device is different from at least one of the patterns of the plurality of fastener holes in the head regions of the first and second devices.

Illustrative embodiment 10A. The kit of any of Illustrative embodiments 7-10, wherein at least one fastener hole in the shaft region of each of the first and second devices comprises at least one combination hole.

Illustrative embodiment 10B. The kit of Illustrative embodiment 10A, wherein the shaft region of at least one of the first and second devices comprises a plurality of combination fastener holes.

Illustrative embodiment 10C. The kit of Illustrative embodiment 10A or 10B, wherein the shaft region comprises between one (1) to twelve (12) combination fastener holes.

Illustrative embodiment 10D. The kit of Illustrative embodiment 10B or 10C, wherein the plurality of combination fastener holes extends substantially linearly along the longitudinal axis of the shaft region.

Illustrative embodiment 10E. The kit of any of Illustrative embodiments 7-10D, wherein the shaft region of at least one of the first and second devices comprises at least one combination fastener hole and at least one single fastener hole.

Illustrative embodiment 10F. The kit of Illustrative embodiment 10E, wherein the shaft region comprises a plurality of combination fastener holes and a plurality of single fastener holes.

Illustrative embodiment 10G. The kit of Illustrative embodiment 10E or 10F, wherein the shaft region comprises from 1 to 20 combination fastener holes and from 1 to 20 single fastener holes.

Illustrative embodiment 11. The kit of any of Illustrative embodiments 9-10G, further comprising at least one first bone plate device, at least two second bone plate devices, and at least one third bone plate device.

Illustrative embodiment 12. The kit of any of Illustrative embodiments 9-11, further comprising at least two first bone plate devices, at least two second bone plate devices, and at least two third bone plate devices, wherein the at least two first devices have the same head region as each other but different shaft region lengths, the at least two second devices have the same head region as each other but different shaft region lengths, and the at least two third devices have the same head region as each other but different shaft region lengths.

Illustrative embodiment 13. The kit of any of Illustrative embodiments 7-12, further comprising: a plurality of bone fasteners that matingly engages the plurality of fastener holes in the head region of the device; and/or at least one bone fastener that matingly engages the at least one fastener hole in the shaft region of the device.

Illustrative embodiment 14. The kit of any of Illustrative embodiments 7-13, further comprising at least one component selected from the group consisting of a guide block, an aiming device, a Kirschner wire, a sizing template, a sharp hook, a sleeve, a washer, a nut, a length probe, a depth gauge, a drill guide, a drill bit, a screwdriver (or portion thereof), a ratchet, a torque limiter, an extraction screw, and combinations thereof.

Illustrative embodiment 15. A method of promoting healing of a fracture in the humerus of a subject, the method comprising the steps of: placing a bone plate device adjacent a surface of the fractured proximal humerus, wherein the bone plate device comprises: a shaft region comprising an elongated portion extending along a longitudinal axis, the shaft region having an upper surface, an opposed bone-facing surface, a lower edge, a first side edge, a second side edge, and a width extending between the first and second side edges, and wherein the shaft region has at least one fastener hole extending through the upper surface and bone-facing surface for receiving at least one bone fastener; and a head region extending at a lateral angle relative to the longitudinal axis, the head region having an upper surface, an opposed bone-facing surface, an upper boundary edge with a curvature, a first side edge, and a second side edge, the head region having a curved bone-facing surface with a radius of curvature that approximately conforms to a shape of the greater tuberosity, wherein the head region has a maximum width extending between the first or second side edge and a lower end of the upper boundary edge, wherein the head region has a ratio of maximum width to height in a range of from about 1.2:1 to about 1.5:1, and wherein the head region comprises a plurality of fastener holes extending through the upper surface and bone-facing surface for receiving bone fasteners; securing the bone plate device to the fractured humeral bone by inserting bone fasteners through the fastener holes in the bone plate device and through the bone plate device into the bone such that the head region of the bone plate device is attached to a greater tuberosity of the proximal humerus and the shaft region of the bone plate device is attached to a shaft of the humerus, and wherein the head region is secured to the greater tuberosity such that the upper edge curvature of the head region is disposed substantially adjacent an upper curvature of the greater tuberosity.

Illustrative embodiment 16. The method of Illustrative embodiment 15, further comprising the step of selecting the bone plate device from a kit of bone plate devices, wherein the head regions of at least two of the bone plate devices of the kit have different sizes and/or shapes.

Illustrative embodiment 16A. The method of Illustrative embodiment 16, wherein the kit is the kit of any of Illustrative embodiments 7-14.

Illustrative embodiment 17. The method of any of Illustrative embodiments 16 or 16A, further comprising the step of performing a plurality of morphological measurements of the humerus to determine which bone plate device to select.

Illustrative embodiment 18. The method of Illustrative embodiment 17, wherein the plurality of morphological measurements comprises a greater tuberosity top point, a greater tuberosity/shaft connection point, a greater tuberosity maximum anterior point, and a greater tuberosity maximum posterior point, and wherein the height of the head region is calculated as a distance between the greater tuberosity top point and the greater tuberosity/shaft connection point, and the maximum width is calculated as a distance between the greater tuberosity maximum anterior point and the greater tuberosity maximum posterior point.

Illustrative embodiment 18A. The method of any of Illustrative embodiments 15-18, wherein the head region of the bone plate device has a ratio of maximum width to height in a range of from about 1.25:1 to about 1.35:1.

Illustrative embodiment 18B. The method of Illustrative embodiment 18A, wherein the head region of the bone plate device has a ratio of maximum width to height in a range of from about 1.27:1 to about 1.33:1.

Illustrative embodiment 18C. The method of any of Illustrative embodiments 15-18, wherein the head region has a ratio of maximum width to height in a range of from about 1.3:1 to about 1.44:1.

Illustrative embodiment 18D. The method of Illustrative embodiment 18C, wherein the head region of the bone plate device has a ratio of maximum width to height in a range of from about 1.38:1 to about 1.42:1.

Illustrative embodiment 19. The method of any of Illustrative embodiments 15-18D, wherein the head region has a maximum width in a range of from about 22 mm to about 29 mm and a maximum radius of curvature in a range of from about 17 mm to about 23 mm.

Illustrative embodiment 20. The method of any of Illustrative embodiments 15-19, wherein the plurality of fastener holes in the head region of the bone plate device has a pattern comprising an upper row of three holes, a middle row of two holes, and a lower row of two holes.

Illustrative embodiment 20A. The method of Illustrative embodiment 20, wherein at least one of the rows of holes is disposed along the lateral angle.

Illustrative embodiment 20B. The method of Illustrative embodiment 20 or 20A, wherein the upper row comprises the at least three holes disposed along a first angled line.

Illustrative embodiment 20C. The method of Illustrative embodiment 20B, wherein the middle row comprises the at least two holes disposed along a second angled line.

Illustrative embodiment 20D. The method of Illustrative embodiment 20C, wherein the lower row comprises the at least two holes disposed along a third angled line.

Illustrative embodiment 20E. The method of Illustrative embodiment 20D, wherein the first, second, and third angled lines are substantially parallel.

Illustrative embodiment 20F. The method of any of Illustrative embodiments 20-20E, wherein the upper row is configured to be adjacent an upper ¼th to ⅓rd of a humeral head, the middle row is configured to be adjacent a middle of the humeral head, and the lower row is configured to be adjacent a calcar.

Illustrative embodiment 20G. The method of any of Illustrative embodiments 20-20F, wherein the upper row comprises three holes, the middle row comprises 2-3 holes, and the lower row comprises 2-3 holes.

Illustrative embodiment 20H. The method of any of Illustrative embodiments 15-20G, wherein at least one fastener hole in the shaft region comprises at least one combination hole.

Illustrative embodiment 20I. The method of Illustrative embodiment 20H, wherein the shaft region comprises a plurality of combination fastener holes.

Illustrative embodiment 20J. The method of Illustrative embodiment 20H or 20I, wherein the shaft region comprises between one (1) to twelve (12) combination fastener holes.

Illustrative embodiment 20K. The method of Illustrative embodiment 20I or 20K, wherein the plurality of combination fastener holes extends substantially linearly along the longitudinal axis of the shaft region.

Illustrative embodiment 20L. The method of any of Illustrative embodiments 15-20K, wherein the shaft region comprises at least one combination fastener hole and at least one single fastener hole.

Illustrative embodiment 20M. The method of Illustrative embodiment 20L, wherein the shaft region comprises a plurality of combination fastener holes and a plurality of single fastener holes.

Illustrative embodiment 20N. The method of Illustrative embodiment 20L or 20M, wherein the shaft region comprises from 1 to 20 combination fastener holes and from 1 to 20 single fastener holes.

Thus, in accordance with the present disclosure, there have been provided devices, assemblies, kits, and systems, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A bone plate device configured and adapted to be attached to a surface of a proximal humerus for promoting healing of a fracture in the humerus of a subject, the device comprising:

a shaft region comprising an elongated portion extending along a longitudinal axis, the shaft region configured and adapted to be attached to a shaft of the humerus, the shaft region having an upper surface, an opposed bone-facing surface, a lower edge, a first side edge, a second side edge, and a width extending between the first and second side edges, and wherein the shaft region has at least one fastener hole extending through the upper surface and bone-facing surface for receiving at least one bone fastener adapted and configured to secure the shaft region of the bone plate device to the shaft of the humerus; and a head region configured to conform to and adapted to be attached to a greater tuberosity of the proximal humerus, the head region extending at a lateral angle relative to the longitudinal axis, the head region having an upper surface, an opposed bone-facing surface, an upper boundary edge with a curvature, a first side edge, and a second side edge, the head region having a curved bone-facing surface with a radius of curvature that approximately conforms to a shape of the greater tuberosity, wherein the head region has a maximum width extending between the first or second side edge and a lower end of the upper boundary edge, wherein the head region has a ratio of maximum width to height in a range of from about 1.2:1 to about 1.5:1, and wherein the head region comprises a plurality of fastener holes extending through the upper surface and bone-facing surface for receiving bone fasteners adapted and configured to secure the head region to the greater tuberosity such that the upper edge curvature of the head region is adapted and configured to be disposed substantially adjacent an upper curvature of the greater tuberosity.

2. The device of claim 1, wherein the size and configuration of the bone plate device are adapted and configured to a plurality of morphological measurements of the greater tuberosity of the humerus, wherein the morphological measurements comprise a greater tuberosity top point, a greater tuberosity/shaft connection point, a greater tuberosity maximum anterior point, and a greater tuberosity maximum posterior point.

3. The device of claim 2, wherein the height of the head region is adapted and configured to a distance between the greater tuberosity top point and the greater tuberosity/shaft connection point, and wherein the maximum width is adapted and configured to a distance between the greater tuberosity maximum anterior point and the greater tuberosity maximum posterior point.

4. The device of claim 1, wherein the head region has a maximum width in a range of from about 22 mm to about 29 mm and a maximum radius of curvature in a range of from about 17 mm to about 23 mm.

5. The device of claim 1, wherein the plurality of fastener holes in the head region has a pattern comprising an upper row of at least three holes, a middle row of at least two holes, and a lower row of at least two holes.

6. The device of claim 5, wherein at least one of the rows of holes is disposed along the lateral angle.

7. A kit, comprising:

at least a first bone plate device configured and adapted to be attached to a surface of a proximal humerus; and at least a second bone plate device configured and adapted to be attached to a surface of a proximal humerus; and wherein each of the first and second devices is a device of claim 1; and wherein at least the head regions of the first and second devices have different sizes and/or shapes.

8. The kit of claim 7, wherein a pattern of the plurality of fastener holes in the head region of the first device is different from a pattern of the plurality of fastener holes in the head region of the second device.

9. The kit of claim 7, further comprising at least a third bone plate device configured and adapted to be attached to a surface of a proximal humerus, wherein at least the head region of the third device has a different size and/or shape than the first and second devices.

10. The kit of claim 9, wherein a pattern of the plurality of fastener holes in the head region of the third device is different from at least one of the patterns of the plurality of fastener holes in the head regions of the first and second devices.

11. The kit of claim 9, further comprising at least one first bone plate device, at least two second bone plate devices, and at least one third bone plate device.

12. The kit of claim 9, further comprising at least two first bone plate devices, at least two second bone plate devices, and at least two third bone plate devices, wherein the at least two first devices have the same head region as each other but different shaft region lengths, the at least two second devices have the same head region as each other but different shaft region lengths, and the at least two third devices have the same head region as each other but different shaft region lengths.

13. The kit of claim 7, further comprising:

a plurality of bone fasteners that matingly engages the plurality of fastener holes in the head region of the device; and at least one bone fastener that matingly engages the at least one fastener hole in the shaft region of the device.

14. The kit of claim 7, further comprising at least one component selected from the group consisting of a guide block, an aiming device, a Kirschner wire, a sizing template, a sharp hook, a sleeve, a washer, a nut, a length probe, a depth gauge, a drill guide, a drill bit, a screwdriver (or portion thereof), a ratchet, a torque limiter, an extraction screw, and combinations thereof.

15. A method of promoting healing of a fracture in the humerus of a subject, the method comprising the steps of:

placing a bone plate device adjacent a surface of the fractured proximal humerus, wherein the bone plate device comprises:

a shaft region comprising an elongated portion extending along a longitudinal axis, the shaft region having an upper surface, an opposed bone-facing surface, a lower edge, a first side edge, a second side edge, and a width extending between the first and second side edges, and wherein the shaft region has at least one fastener hole extending through the upper surface and bone-facing surface for receiving at least one bone fastener; and a head region extending at a lateral angle relative to the longitudinal axis, the head region having an upper surface, an opposed bone-facing surface, an upper boundary edge with a curvature, a first side edge, and a second side edge, the head region having a curved bone-facing surface with a radius of curvature that approximately conforms to a shape of the greater tuberosity, wherein the head region has a maximum width extending between the first or second side edge and a lower end of the upper boundary edge, wherein the head region has a ratio of maximum width to height in a range of from about 1.2:1 to about 1.5:1, and wherein the head region comprises a plurality of fastener holes extending through the upper surface and bone-facing surface for receiving bone fasteners;

securing the bone plate device to the fractured humeral bone by inserting bone fasteners through the fastener holes in the bone plate device and through the bone plate device into the bone such that the head region of the bone plate device is attached to a greater tuberosity of the proximal humerus and the shaft region of the bone plate device is attached to a shaft of the humerus, and wherein the head region is secured to the greater tuberosity such that the upper edge curvature of the head region is disposed substantially adjacent an upper curvature of the greater tuberosity.

16. The method of claim 15, further comprising the step of selecting the bone plate device from a kit of bone plate devices, wherein the head regions of at least two of the bone plate devices of the kit have different sizes and/or shapes.

17. The method of claim 16, further comprising the step of performing a plurality of morphological measurements of the humerus to determine which bone plate device to select.

18. The method of claim 17, wherein the plurality of morphological measurements comprises a greater tuberosity top point, a greater tuberosity/shaft connection point, a greater tuberosity maximum anterior point, and a greater tuberosity maximum posterior point, and wherein the height of the head region is calculated as a distance between the greater tuberosity top point and the greater tuberosity/shaft connection point, and the maximum width is calculated as a distance between the greater tuberosity maximum anterior point and the greater tuberosity maximum posterior point.

19. The method of claim 15, wherein the head region has a maximum width in a range of from about 22 mm to about 29 mm and a maximum radius of curvature in a range of from about 17 mm to about 23 mm.

20. The method of claim 15, wherein the plurality of fastener holes in the head region of the bone plate device has a pattern comprising an upper row of three holes, a middle row of two holes, and a lower row of two holes, and wherein at least one of the rows of holes is disposed along the lateral angle.

* * * * *